US007884104B2

(12) United States Patent
Cox et al.

(10) Patent No.: US 7,884,104 B2
(45) Date of Patent: Feb. 8, 2011

(54) AMINOPIPERIDINES AS DIPEPTIDYL PEPTIDASE-IV INHIBITORS FOR THE TREATMENT OR PREVENTION OF DIABETES

(75) Inventors: Jason M. Cox, East Windsor, NJ (US); Scott D. Edmondson, Clark, NJ (US); Bart Harper, New York, NJ (US); Ann E. Weber, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 999 days.

(21) Appl. No.: 11/662,064

(22) PCT Filed: Sep. 27, 2005

(86) PCT No.: PCT/US2005/034775
§ 371 (c)(1),
(2), (4) Date: Mar. 6, 2007

(87) PCT Pub. No.: WO2006/039325
PCT Pub. Date: Apr. 13, 2006

(65) Prior Publication Data
US 2008/0076773 A1 Mar. 27, 2008

Related U.S. Application Data

(60) Provisional application No. 60/615,478, filed on Oct. 1, 2004.

(51) Int. Cl.
*A61K 31/4545* (2006.01)
*C07D 487/04* (2006.01)

(52) U.S. Cl. .................. 514/250; 514/248; 514/249; 514/252.03; 514/255.05; 514/256; 514/259.3; 514/264.1; 514/275; 514/303; 514/313; 514/318; 544/236; 544/238; 544/279; 544/326; 544/328; 544/350; 544/405; 546/118; 546/159; 546/173; 546/194

(58) Field of Classification Search .................. 514/248, 514/249, 250, 252.03, 255.05, 256, 259.3, 514/264.1, 275, 303, 310, 313, 318; 544/236, 544/238, 279, 326, 328, 350, 405; 546/118, 546/173, 159, 194
See application file for complete search history.

(56) References Cited

U.S. PATENT DOCUMENTS

| 6,869,947 | B2 * | 3/2005 | Kanstrup et al. ....... 514/217.06 |
| 7,683,079 | B2 * | 3/2010 | Boehringer et al. ......... 514/329 |
| 2005/0148606 | A1 | 7/2005 | Kanstrup et al. |
| 2006/0019975 | A1 * | 1/2006 | Humphrey et al. ..... 514/266.22 |
| 2006/0135512 | A1 | 6/2006 | Boehringer et al. |
| 2006/0135561 | A1 | 6/2006 | Boehringer et al. |

FOREIGN PATENT DOCUMENTS

| WO | WO 97/03986 | 2/1997 |
| WO | WO 02/076450 A1 | 10/2002 |
| WO | WO 03/000180 A2 | 1/2003 |
| WO | WO 03/000181 A2 | 1/2003 |
| WO | WO 03/004498 A1 | 1/2003 |
| WO | WO 03/082817 A2 | 10/2003 |
| WO | WO 2004/007468 A1 | 1/2004 |
| WO | WO 2004/032836 A2 | 4/2004 |
| WO | WO 2004/037169 A2 | 5/2004 |
| WO | WO 2004/043940 A1 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 A1 | 12/2004 |
| WO | WO 2004/112701 A2 | 12/2004 |
| WO | WO 2005/011581 A2 | 2/2005 |
| WO | WO 2005/044195 A2 | 5/2005 |
| WO | WO 2005/108382 A1 | 11/2005 |
| WO | WO 2005/116029 A1 | 12/2005 |
| WO | WO 2006/066747 A1 | 6/2006 |
| WO | WO 2006/066770 A1 | 6/2006 |

OTHER PUBLICATIONS

Jordan, V. C. Nature Reviews: Drug Discovery, 2, 2003, p. 205.*
Dorwald, F. Zaragoza. Side Reactions in Organic Synthesis: A Guide to Successful Synthesis Design, Weinheim: WILEY-VCH Verlag GmbH & Co. KGaA, 2005, Preface.*
Holst, J. J., "Treatment of Type 2 diabetes mellitus with agonists of the GLP-1 receptor or DPP-IV inhibitors" Expert Opin. Emerg. Drugs, vol. 9, No. 1, pp. 155-166, 2004.
Deacon, C. F. et al., "Inhibitors of dipeptidyl peptidase IV: a novel approach for the prevention and treatment of Type 2 diabetes?" Expert Opin Investig Drugs, vol. 13, No. 9, pp. 1091-1102, 2004.
Augustyns, K. et al., "Dipeptidyl peptidase IV inhibitors as new therapeutic agents for the treatment of Type 2 diabetes", Expert Opin. Ther. Patents, vol. 13, No. 4, pp. 499-510, 2003.
"Novel N-substituted-2-cyanopyrrolidines as potent inhibitors of dipeptidyl peptidase IV in the treatment of non-insulin-dependent diabetes mellitus" Exp. Opin. Ther. Patents, vol. 10, No. 12, pp. 1937-1942, 2000.
Drucker, D. J., "Therapeutic potential of dipeptidyl peptidase IV inhibitors for the treatment of type 2 diabetes", Expert Opin. Investig. Drugs, vol. 12, No. 1, pp. 87-100, 2003.
Vahl, T. P. et al., "Gut peptides in the treatment of diabetes mellitus" Expert Opin. Investig. Drugs, vol. 13, No. 3, pp. 177-188, 2004.

(Continued)

*Primary Examiner*—Celia Chang
(74) *Attorney, Agent, or Firm*—Janet E. Fair; John C. Todaro

(57) ABSTRACT

The present invention is directed to novel substituted aminopiperidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

15 Claims, No Drawings

OTHER PUBLICATIONS

Weber, A. E., "Dipeptidyl Peptidase IV Inhibitors for the Treatment of Diabetes" J. Med. Chem, vol. 47, pp. 4135-4141, 2004.

Holst, J. J. et al., "Glucagon-like peptide 1 and inhibitors of dipeptidyl peptidase IV in the treatment of type 2 diabetes mellitus" Current Opinion in Pharmacology, vol. 4, pp. 589-596, 2004.

Deacon, C. F., "Perspectives in Diabetes—Therapeutic Strategies Based on Glucagon-Like Peptide 1" Diabetes, vol. 53, pp. 2181-2189, 2004.

Augustyns, K. et al., "Inhibitors of proline-specific dipeptidyl peptidases: DPP IV inhibitors as a novel approach for the treatment of Type 2 diabetes" Expert Opin. Ther. Patents, vol. 15, No. 10, pp. 1387-1407, 2005.

Demuth, H.U. et al., "Type 2 diabetes—Therapy with dipeptidyl peptidase IV inhibitors" Biochimica et Biophysica Acta, vol. 1751, pp. 33-44, 2005.

* cited by examiner

AMINOPIPERIDINES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US2005/034775, filed 27 Sep. 2005, which claims the benefit under 35 U.S.C. 119(e) of U.S. Provisional Application No. 60/615,478, filed 1 Oct. 2004.

FIELD OF THE INVENTION

The present invention relates to novel substituted aminopiperidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DPP-IV") enzyme are under investigation as drugs that may be useful in the treatment of diabetes, and particularly Type 2 diabetes. See, for example, international patent publications WO 97/40832; WO 98/19998; WO 01/68603; WO 02/38541; WO 02/076450; WO 03/000180; WO 03/000181; WO 03/024942; WO 03/033524; WO 03/035057; WO 03/035067; WO 03/037327; WO 03/074500; WO 03/082817; WO 04/007468; WO 04/018467; WO 04/026822; WO 04/032836; WO 04/037181; WO 04/041795; WO 04/043940; WO 04/046106; WO 04/050022; WO 04/058266; WO 04/064778; WO 04/069162; WO 04/071454; U.S. Pat. Nos. 5,939,560; 6,011,155; 6,107,317; 6,110,949; 6,166,063; 6,124,305; 6,303,661; 6,432,969; 6,617,340; and 6,699,871; *Bioorg. Med. Chem. Lett.*, 6: 1163-1166 (1996); and *Bioorg. Med. Chem. Lett.* 6: 2745-2748 (1996); for a description of different structural classes of DPP-IV inhibitors. The usefulness of DPP-IV inhibitors in the treatment of Type 2 diabetes is based on the fact that DPP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

DPP-IV inhibitors also have other therapeutic utilities, as discussed herein. DPP-IV inhibitors have not been studied extensively for utilities other than diabetes. New compounds are needed so that improved DPP-IV inhibitors can be found for the treatment of diabetes and potentially other diseases and conditions. The therapeutic potential of DPP-IV inhibitors for the treatment of Type 2 diabetes is discussed by D. J. Drucker in *Exp. Opin. Invest. Drugs,* 12: 87-100 (2003); by K. Augustyns, et al., in *Exp. Opin. Ther. Patents,* 13: 499-510 (2003); and by C. F. Deacon, et al., in *Exp. Opin. Investig. Drugs,* 13: 1091-1102 (2004).

SUMMARY OF THE INVENTION

The present invention is directed to novel substituted aminopiperidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to substituted aminopiperidines that are useful as inhibitors of dipeptidyl peptidase-IV. Compounds of the present invention are described by structural formula I:

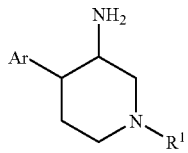

and pharmaceutically acceptable salts thereof; wherein each n is independently 0, 1, 2 or 3;

Ar is phenyl unsubstituted or substituted with one to five $R^3$ substituents;

each $R^3$ is independently selected from the group consisting of
  halogen,
  cyano,
  hydroxy,
  $C_{1-6}$ alkyl, unsubstituted or substituted with one to five halogens, and
  $C_{1-6}$ alkoxy, unsubstituted or substituted with one to five halogens;

$R^1$ is heteroaryl unsubstituted or substituted with one to four $R^2$ substituents;

each $R^2$ is independently selected from the group consisting of
  hydroxy,
  halogen,
  cyano,
  nitro,
  $C_{1-10}$ alkoxy, wherein alkoxy is unsubstituted or substituted with one to five substituents independently selected from halogen or hydroxy,
  $C_{1-10}$ alkyl, wherein alkyl is unsubstituted or substituted with one to five substituents independently selected from halogen or hydroxy,
  $C_{2-10}$ alkenyl, wherein alkenyl is unsubstituted or substituted with one to five substituents independently selected from halogen or hydroxy,
  $(CH_2)_n$-aryl, wherein aryl is unsubstituted or substituted with one to five substituents independently selected hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$—$C_{3-6}$ cycloalkyl, wherein cycloalkyl is unsubstituted or substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$—COOH,
  $(CH_2)_n$—COOC$_{1-6}$ alkyl,
  $(CH_2)_n$—NR$^4$R$^5$,
  $(CH_2)_n$—CONR$^4$R$^5$,
  $(CH_2)_n$—OCONR$^4$R$^5$,
  $(CH_2)_n$—SO$_2$NR$^4$R$^5$,
  $(CH_2)_n$—SO$_2$R$^6$,
  $(CH_2)_n$—NR$^7$SO$_2$R$^6$,
  $(CH_2)_n$—NR$^7$CONR$^4$R$^5$,
  $(CH_2)_n$—NR$^7$COR$^7$, and
  $(CH_2)_n$—NR$^7$CO$_2$R$^6$;

wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

$R^4$ and $R^5$ are each independently selected from the group consisting of
  hydrogen,
  $(CH_2)_n$-phenyl,
  $(CH_2)_n$—$C_{3-6}$ cycloalkyl, and
  $C_{1-6}$ alkyl;

wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^4$ and $R^5$ substituents together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;

each $R^6$ is independently $C_{1-6}$ alkyl, wherein alkyl is unsubstituted or substituted with one to five substituents independently selected from halogen and hydroxyl; and $R^7$ is hydrogen or $R^6$.

In one embodiment of the compounds of the present invention, $R^3$ is selected from the group consisting of fluorine, chlorine, bromine, methyl, trifluoromethyl, and trifluoromethoxy. In a class of this embodiment, $R^3$ is fluorine, chlorine, methyl, or trifluoromethyl.

In a second embodiment of the compounds of the present invention, $R^1$ is a heteroaryl group selected from the group consisting of:

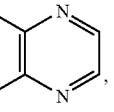

wherein the heteroaryl group is unsubstituted or substituted with one to four $R^2$ substituents.

In a class of this embodiment, $R^1$ is selected from the group consisting of:

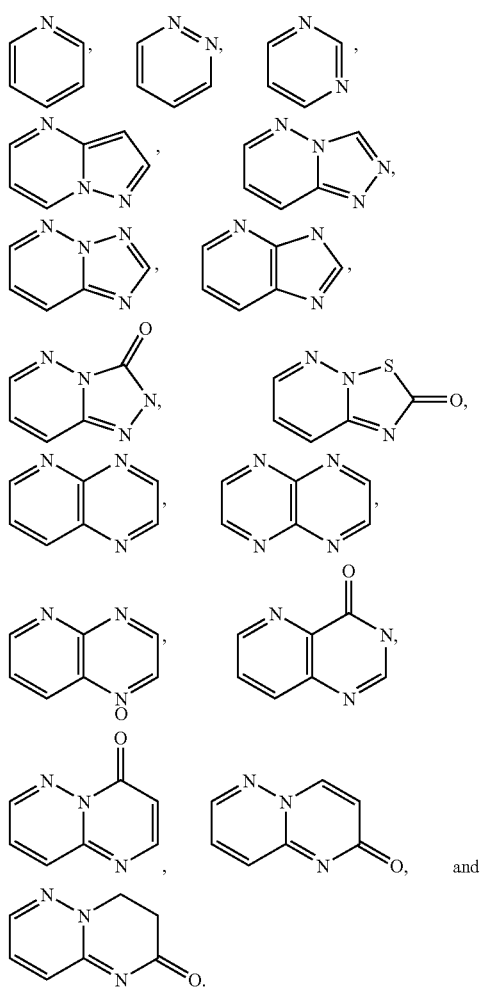

In a subclass of this class, $R^1$ is selected from the group consisting of:

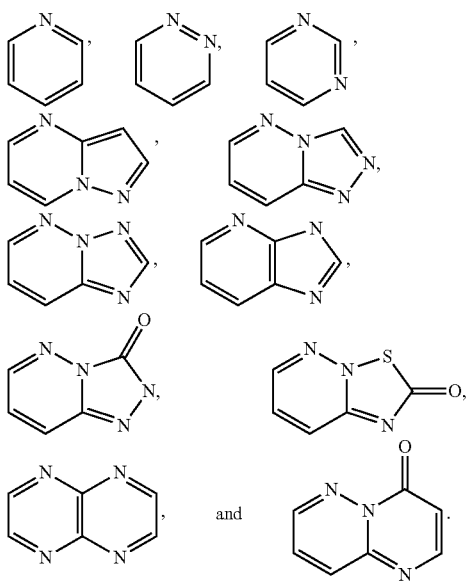

In a subclass of this subclass, $R^1$ is selected from the group consisting of:

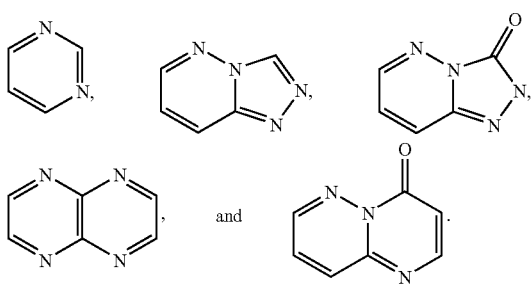

In a third embodiment of the compounds of the present invention, $R^2$ is selected from the group consisting of
halogen,
cyano,
nitro,
$C_{1-10}$ alkoxy, wherein alkoxy is unsubstituted or substituted with one to five substituents independently selected from halogen or hydroxy,
$C_{1-10}$ alkyl, wherein alkyl is unsubstituted or substituted with one to five substituents independently selected from halogen or hydroxy,
aryl, wherein aryl is unsubstituted or substituted with one to five substituents independently selected hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
heteroaryl, wherein heteroaryl is unsubstituted or substituted with one to three substituents independently selected from hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
$C_{3-6}$ cycloalkyl, wherein cycloalkyl is unsubstituted or substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
COOH, and
$COOC_{1-6}$ alkyl.

In a class of this embodiment, $R^2$ is selected from the group consisting of:

fluoro, chloro, cyano, nitro, $C_{1-4}$ alkyl, trifluoromethyl, methoxy, 4-fluorophenyl, cyclohexyl, cyclopropyl, ethoxycarbonyl, carboxy, furyl, pyridyl, and thienyl.

In a fourth embodiment of the compounds of the present invention, there are provided compounds of structural formulae Ia and Ib of the indicated stereochemical configuration having a trans orientation of the Ar and $NH_2$ substituents on the two stereogenic piperidine carbon atoms marked with an *:

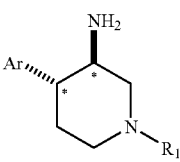
(Ia)

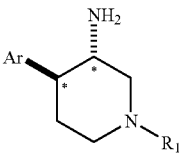
(Ib)

wherein Ar and $R^1$ are as described above.

In a class of this fourth embodiment, there are provided compounds of structural formula Ia of the indicated absolute stereochemical configuration having a trans orientation of the Ar and $NH_2$ substituents on the two stereogenic piperidine carbon atoms marked with an *:

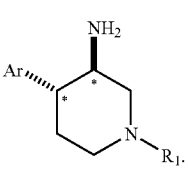
(Ia)

In a subclass of this class, Ar is phenyl unsubstituted or substituted with one to three $R^3$ substituents independently selected from fluorine, chlorine, methyl, and trifluoromethyl; and $R^1$ is a heteroaryl group selected from the group consisting of:

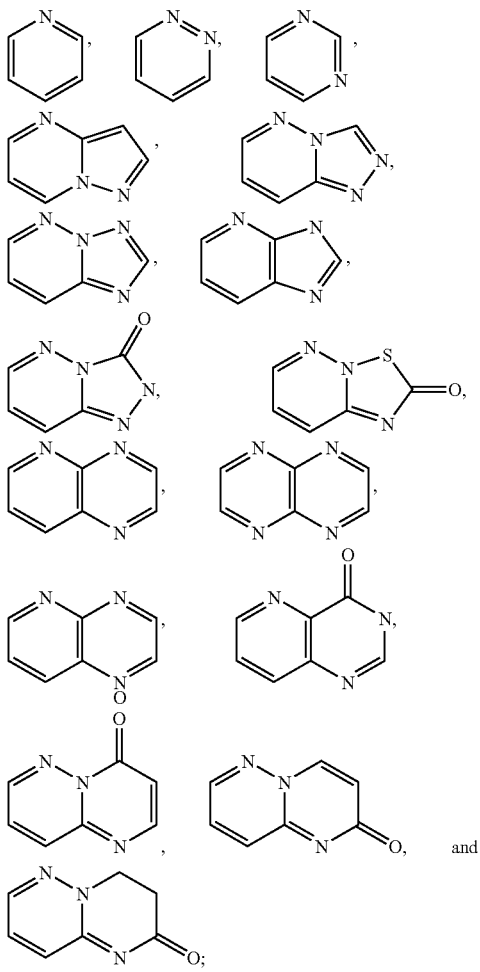

wherein said heteroaryl group is unsubstituted or substituted with one to two $R^2$ substituents independently selected from the group consisting of:

fluoro, chloro, cyano, nitro, $C_{1-4}$ alkyl, trifluoromethyl, methoxy, 4-fluorophenyl, cyclohexyl, cyclopropyl, ethoxycarbonyl, carboxy, furyl, pyridyl, and thienyl.

In a subclass of this subclass, $R^1$ is selected from the group consisting of:

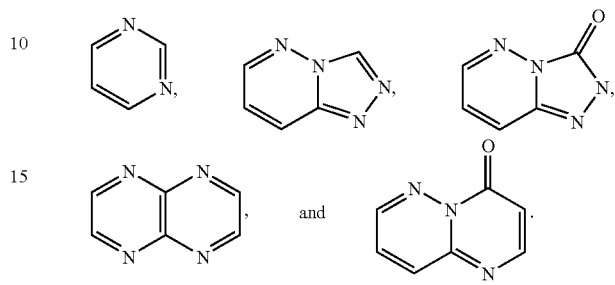

Nonlimiting examples of compounds of the present invention that are useful as dipeptidyl peptidase-IV inhibitors are the following structures having the indicated absolute stereochemical configurations at the two stereogenic piperidine carbon atoms:

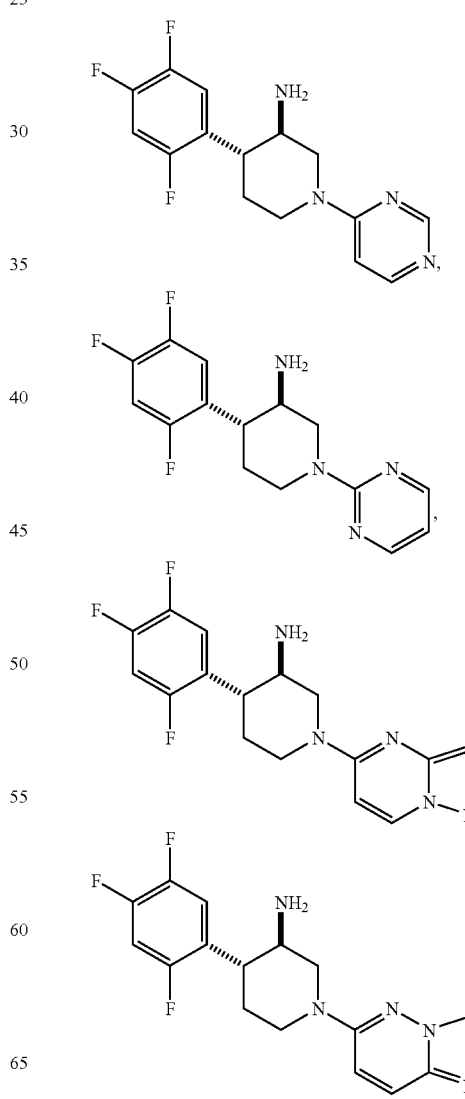

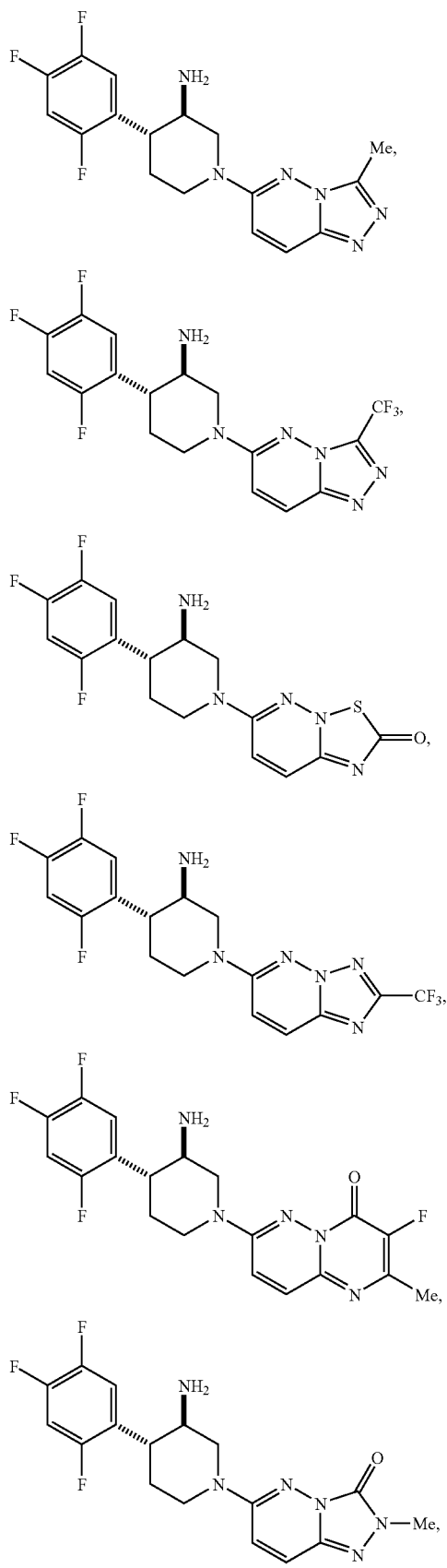
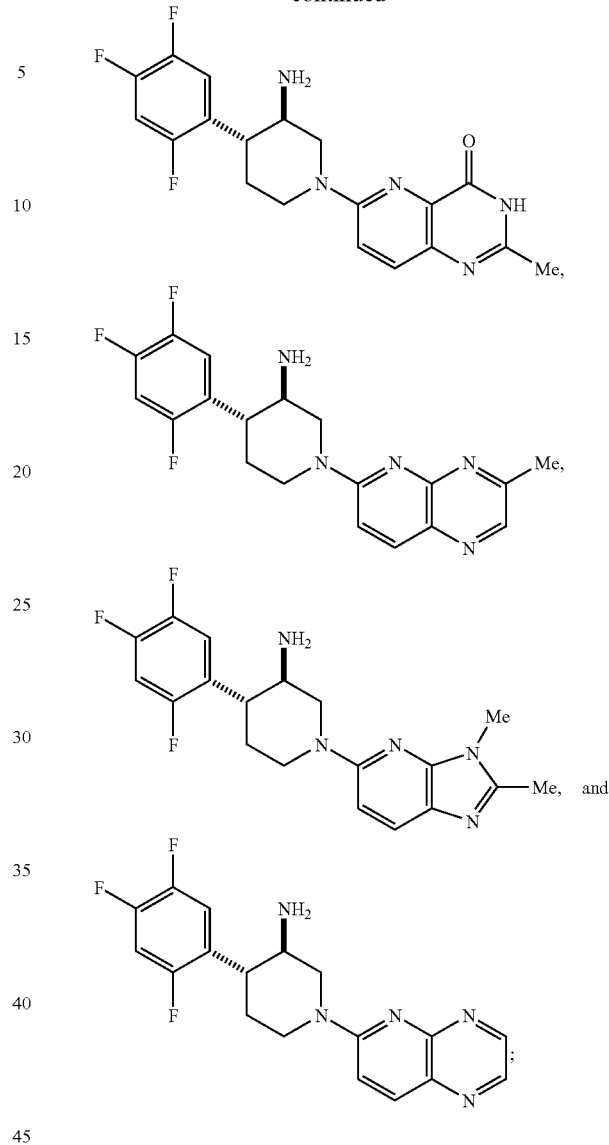

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

The term "cycloalkyl" refers to a saturated hydrocarbon containing one ring having a specified number of carbon atoms. Examples of cycloalkyl include cyclopropyl (cPr), cyclobutyl, cyclopentyl, cyclohexyl, cycloheptyl, cyclooctyl, and the like. A cycloalkyl group is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heterocyclyl" refers to saturated or unsaturated non-aromatic rings or ring systems containing at least one heteroatom selected from O, S and N, further including the oxidized forms of sulfur, namely SO and SO$_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, pteridinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, imidazo[4,5-b]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, imidazo[1,2-a]pyrimidinyl, imidazo[1,5-a]pyrimidinyl, imidazo[4,5-b]pyridyl, pyrazolo[1,5-a]pyrimidinyl, [1,2,4-triazolo][1,5-a]pyrimidinyl, [1,2,4-triazolo][4,3-a]pyrimidinyl, [1,2,3-triazolo][1,5-a]pyrimidinyl, pyrazolo[1,5-b]pyridazinyl, imidazo[1,5-b]pyridazinyl, imidazo[1,2-b]pyridazinyl, [1,2,4-triazolo][4,3-b]pyridazinyl, [1,2,4-triazolo][1,5-b]pyridazinyl, pyrido[2,3-b]pyrazinyl, pyrido[3,2-d]pyrimidinyl, pyrido[2,3-b]pyrimidinyl, pyrido[3,2-d]pyrimidin-4(3H)-one, pyrazino[2,3-b]pyrazinyl, 1-oxido-pyrazino[2,3-b]pyrazinyl, [1,2,4]triazolo[4,3-b]pyridazin-3(2H)-one, [1,2,4]thiadiazolo[2,3-b]pyridazin-2-one, pyridazino[1,6-a][1,3,5]triazin-4-one, pyridazino[1,6-a][1,3,5]triazin-2-one,3,4-dihydro-2H-pyrimido[1,2-b]pyridazine-2-one, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. In particular the compounds of the present invention have an asymmetric center at the stereogenic carbon atoms marked with an * in Formulae Ia and Ib. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formulae Ia and Ib show the preferred stereochemistry at the stereogenic carbon atom to which are attached the Ar and NH$_2$ groups.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-IV to release the fluorescent AMC leaving group. The kinetic parameters that describe this reaction are as follows: $K_m$=50 µM; $k_{cat}$=75 s$^{-1}$; $k_{cat}/K_m$=1.5×10$^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro- AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 μM. Such a result is indicative of the intrinsic activity of the compounds in use as inhibitors the dipeptidyl peptidase-IV enzyme activity.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type 2 Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-IV (eg. PACAP). Inactivation of these peptides by DPP-IV may also play a role in glucose homeostasis. The DPP-IV inhibitors of the present invention therefore have utility in the treatment of Type 2 diabetes and in the treatment and prevention of the numerous conditions that often accompany Type 2 diabetes, including Syndrome X (also known as Metabolic Syndrome), reactive hypoglycemia, and diabetic dyslipidemia. Obesity, discussed below, is another condition that is often found with Type 2 diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-IV inhibitors may also be useful to treat hypertension associated with this condition.

Obesity: DPP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-IV. ICV administration of GLP-2 also inhibits food intake, analogous to the effects observed with GLP-1 (*Nature Medicine*, 6: 802-807 (2000)). In addition, studies with DPP-IV deficient mice suggest that these animals are resistant to diet-induced obesity and associated pathology (e.g. hyperinsulinonemia).

Cardiovascular Disease: GLP-1 has been shown to be beneficial when administered to patients following acute myocardial infarction, leading to improved left ventricular function and reduced mortality after primary angioplasty (*Circulation*, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-IV inhibitors are expected to show similar effects through their ability to stabilize endogenous GLP-1.

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[344]; this is prevented by the DPP-IV inhibitor diprotin A; and (3) GRF[3-44] is found in the plasma of a human GRF transgenic pig (*J. Clin. Invest.*, 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury is suggested by the results of studies indicating that glucagon-like peptide-2 (GLP-2), a likely endogenous substrate for DPP-IV, may exhibit trophic effects on the intestinal epithelium (*Regulatory Peptides* 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-IV inhibitors in in vivo models of disease. DPP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (*Transplantation*, 63: 1495-1500 (1997)). DPP-IV inhibitors have been tested in collagen and alkyldiamine-induced arthritis in rats and showed a statistically significant attenuation of hind paw swelling in this model [*Int. J. Immunopharmacology.* 19:15-24 (1997) and *Immunopharmacology*, 40: 21-26 (1998)]. DPP-IV is upregulated in a number of autoimmune diseases including rheumatoid arthritis, multiple sclerosis, Graves' disease, and Hashimoto's thyroiditis (*Immunology Today* 20: 367-375 (1999)).

HIV Infection: DPP-IV inhibition may be useful for the treatment or prevention of HIV infection or AIDS because a number of chemokines which inhibit HIV cell entry are potential substrates for DPP-IV (*Immunology Today.* 20: 367-375 (1999)). In the case of SDF-1alpha, cleavage decreases antiviral activity (*PNAS*, 95: 6331-6 (1998)). Thus, stabilization of SDF-1alpha through inhibition of DPP-IV would be expected to decrease HIV infectivity.

Hematopoiesis: DPP-IV inhibition may be useful for the treatment or prevention of hematopoiesis because DPP-IV may be involved in hematopoiesis. A DPP-IV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment or prevention of various neuronal or psychiatric disorders because a number of peptides implicated in a variety of neuronal processes are cleaved in vitro by DPP-IV. A DPP-IV inhibitor thus may have a therapeutic benefit in the treatment of neuronal disorders. Endomorphin-2, beta-casomorphin, and substance P have all been shown to be in vitro substrates for DPP-IV. In all cases, in vitro cleavage is highly efficient, with $k_{cat}/K_m$ about $10^6$ $M^{-1}s^{-1}$ or greater. In an electric shock jump test model of analgesia in rats, a DPP-IV inhibitor showed a significant effect that was independent of the presence of exogenous endomorphin-2 (*Brain Research*, 815: 278-286 (1999)). Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DPP-IV have an anxiolytic phenotype (WO 02/34243; Karl et al., *Physiol. Behav.* 2003). DPP-IV deficient mice also have an anxiolytic phenotype using the porsolt and light/dark models. Thus DPP-IV inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-IV inhibitors are expected to show similar effects.

Myocardial Infarction: GLP-1 has been shown to be beneficial when administered to patients following acute myocardial infarction (*Circulation*, 109: 962-965 (2004)). DPP-IV inhibitors are expected to show similar effects through their ability to stabilize endogenous GLP-1.

Tumor Invasion and Metastasis: DPP-IV inhibition may be useful for the treatment or prevention of tumor invasion and metastasis because an increase or decrease in expression of several ectopeptidases including DPP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (*Eur. J. Clin. Chem. Clin. Biochem.* 30: 333-338 (1992)).

Sperm motility/male contraception: DPP-IV inhibition may be useful for the altering sperm motility and for male contraception because in seminal fluid, prostatosomes, prostate derived organelles important for sperm motility, possess very high levels of DPP-IV activity (*Eur. J. Clin. Chem. Clin. Biochem.*, 30: 333-338 (1992)).

Gingivitis: DPP-IV inhibition may be useful for the treatment of gingivitis because DPP-IV activity was found in gingival crevicular fluid and in some studies correlated with periodontal disease severity (*Arch. Oral Biol.*, 37: 167-173 (1992)).

Osteoporosis: DPP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DPP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, and PPARα agonists, such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP nimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297 and muraglitazar, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774;

(q) inhibitors of 11β-hydroxysteroid dehydrogenase type 1, such as those disclosed in U.S. Pat. No. 6,730,690;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); and WO 03/000181 (3 Jan. 2003). Specific DPP-IV inhibitor compounds include isoleucine thiazolidide (P32/98); NVP-DPP-728; LAF 237; P93/01; and BMS 477118.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; and PCT Publication WO 04/048317.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents,* 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science,* 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of the present invention can be prepared from intermediates such as those of formula II and a heteroaryl halide III using standard coupling conditions followed by deprotection. The preparation of these intermediates is described in the following Schemes, wherein Ar and $R^1$ are as defined above, X is Cl, Br, I, triflate, or some other leaving group, and P is a suitable nitrogen protecting group such as tert-butoxycarbonyl (BOC), benzyloxycarbonyl (Cbz), and 9-fluorenylmethoxycarbonyl (Fmoc).

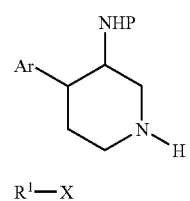

Compounds of formula IIa, wherein P is BOC, may be prepared from intermediate 1 using a route described in Scheme 1. Deprotonation of lactam 1 with a base such as sodium hexamethyldisilazane followed by reaction with benzyl bromide provides the corresponding N-benzyl lactam. Subsequent hydrolysis of the methyl ester with, for example, lithium hydroxide then provides acid 2. Acid 2 may then be subjected to Curtius rearrangement following literature conditions (D. A. Evans, et al. *J. Org. Chem.*, 64: 6411-6417 (1999)) to give the corresponding carboxybenzyl carbamate, which is deprotected under hydrogenation conditions in the presence of di-tert-butyl dicarbonate to provide intermediate 3. Reduction of 3 using borane is followed by acidic work-up and reprotection as the Boc derivative to provide 4. Removal of the benzyl protecting group by catalytic hydrogenation with, for example, hydrogen gas and palladium hydroxide catalyst then provides intermediate IIa.

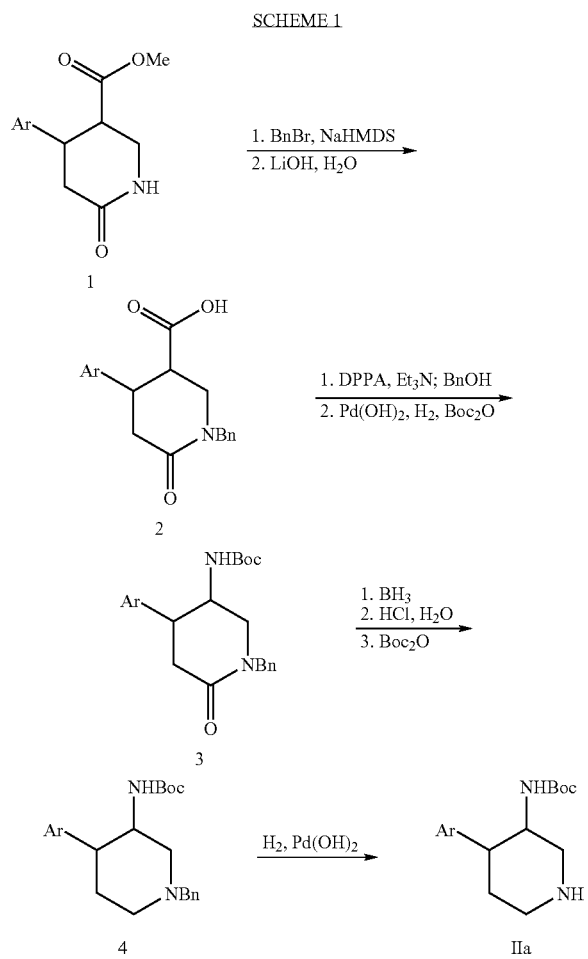

Compounds of formula IIb, wherein P is Cbz, may be prepared from intermediate 1 using a route described in Scheme 2. Treatment of lactam 1 with Meerwein's reagent (trimethyloxonium tetrafluoroborate) provides intermediate 5. Reduction of 5 with sodium borohydride and protection of the amine with, for example, di-tert-butyl dicarbonate provides N-Boc intermediate 6. Ester 6 may be hydrolyzed and then exposed to Curtius rearrangement conditions described above in Scheme 1 to give 7. Deprotection under acidic conditions provides compound IIb.

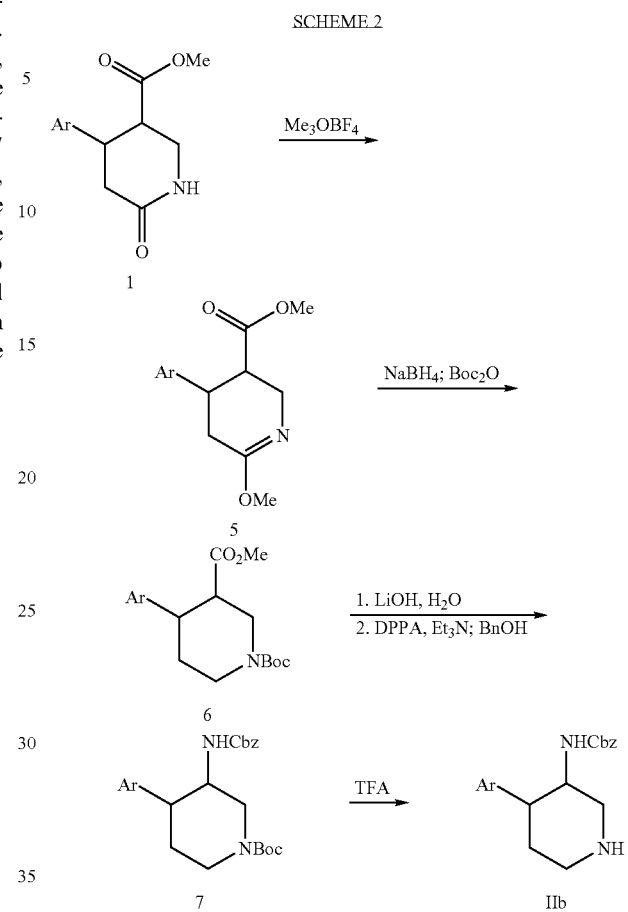

Intermediates of formula 1 are known in the literature or may be conveniently prepared by a variety of methods familiar to those skilled in the art. One route described in the literature (W. H. Moos et al., *J. Org. Chem.*, 46: 5064-5074 (1981)) is illustrated in Scheme 3. A substituted benzaldehyde 8 is treated with trimethyl or triethyl phosphonoacetate 9 in the presence of a base such as 1,8-diazobicyclo[5.4.0]undec-7-ene to provide the aryl enoate 10. Conjugate addition of ethyl or methyl cyanoacetate 11 to enoate 10 in the presence of sodium methoxide provides 12 as a mixture of stereoisomers at each chiral center. Reduction of the cyano group in 12 using catalytic hydrogenation with, for example, hydrogen gas and a platinum (IV) oxide catalyst, is followed by treatment of the product amine with basic methanol to induce cyclization and equilibration of the stereoisomers to predominantly the trans stereoisomer. This may be followed by re-esterification of the intermediate using, for example, trimethylsilyldiazomethane to give compound 1 as predominantly the trans isomer.

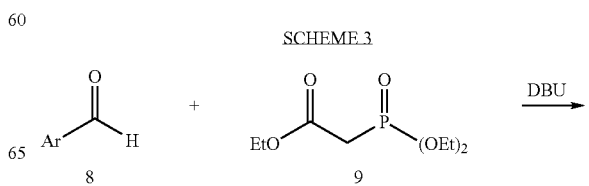

-continued

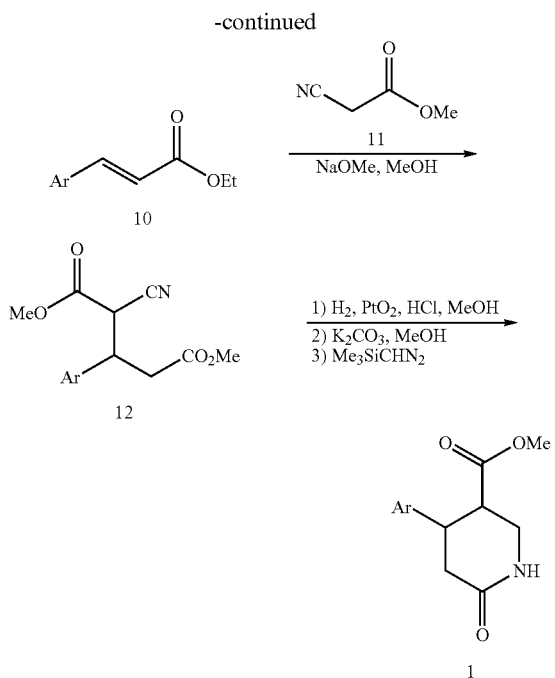

Intermediates III are commercially available, known in the literature, or conveniently prepared by a variety of methods familiar to those skilled in the art. Intermediates Ella may be prepared from 3,6-dichloropyridazine 13 using a variation of a route described in the literature (J. D. Albright, et. al. *J. Med. Chem.* 1981, 24, 592-600) as illustrated in Scheme 4. Alkyl or aryl hydrazides 14, which are commercially available, known in the literature, or conveniently prepared by a variety of methods familiar to those skilled in the art (K. M. Kahn, et. al. *Bioorg. Med. Chem.* 2003, 11, 1381-1387) are heated with 13 in a solvent such as ethanol to provide chloropyridazine-fused triazoles IIIa, wherein $R^2$ is defined above.

SCHEME 4

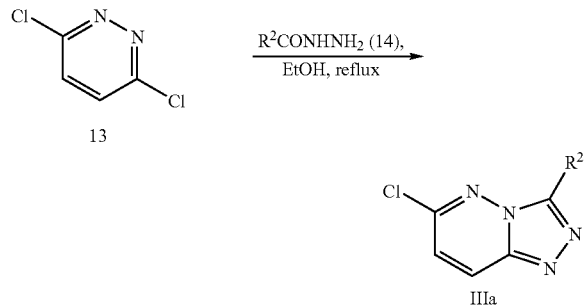

Intermediates IIIb may be prepared from 6-chloropyridazin-3-amine 15 using a variation of a route described in the literature (E. Luraschi, et. al. *Il Farmaco.* 1997, 52, 213-217) as illustrated in Scheme 5. Substituted α-bromoketones 16, which are commercially available or known in the literature, are heated with 15 in a solvent such as ethanol to provide chloropyridazine-fused imidazoles IIIb, wherein $R^2$ is defined above.

SCHEME 5

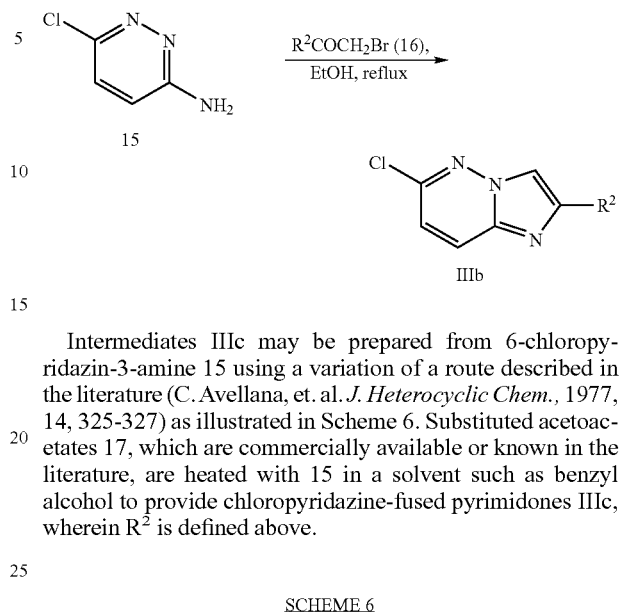

Intermediates IIIc may be prepared from 6-chloropyridazin-3-amine 15 using a variation of a route described in the literature (C. Avellana, et. al. *J. Heterocyclic Chem.*, 1977, 14, 325-327) as illustrated in Scheme 6. Substituted acetoacetates 17, which are commercially available or known in the literature, are heated with 15 in a solvent such as benzyl alcohol to provide chloropyridazine-fused pyrimidones IIIc, wherein $R^2$ is defined above.

SCHEME 6

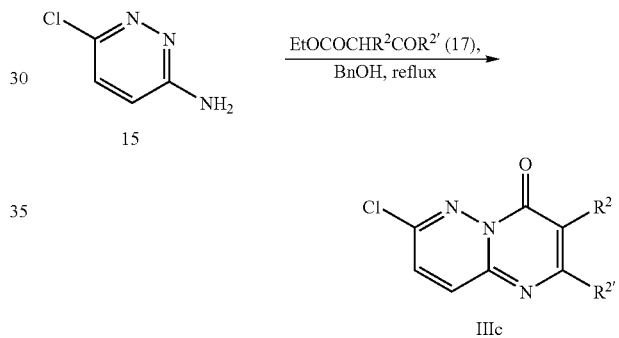

Compounds of Formula I may be prepared as illustrated in Scheme 7 from intermediate II described above and intermediate III, wherein X is Cl, Br, I, triflate, or some other leaving group and $R^1$ is a heteroaryl group, unsubstituted or substituted with one or more $R^2$ substituents, as defined above. Intermediates III are known in the literature or may be conveniently prepared by a variety of methods familiar to those skilled in the art. Intermediates 18 may be prepared by heating II and III together in the presence of a base such as triethylamine or N,N-diisopropylethylamine in solvents such as toluene, N,N-dimethylformamide (DMF), or ethylene glycol dimethyl ether (DME) according to procedures outlined in L. Toma, et. al. *J. Med. Chem.* 2002, 45, 4011-4017 and references contained therein. The protecting group of 18 is then removed with, for example, trifluoroacetic acid or methanolic hydrogen chloride in the case of Boc to give the desired amine I. Alternatively, the protecting group may be removed with, for example, hydrogen bromide in acetic acid or catalytic hydrogenation in the case of Cbz to give the desired amine I. The product is purified from unwanted side products, if necessary, by crystallization, trituration, preparative thin layer chromatography, flash chromatography on silica gel, such as with a Biotage® apparatus, or HPLC. Compounds that are purified by reverse phase HPLC may be isolated as the corresponding salt. Purification of intermediates is achieved in the same manner.

SCHEME 7

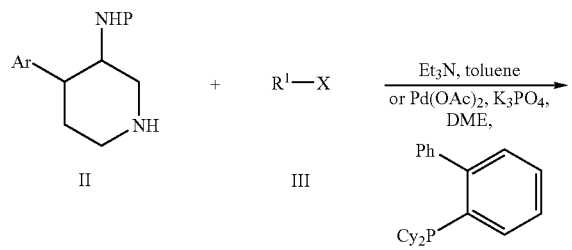

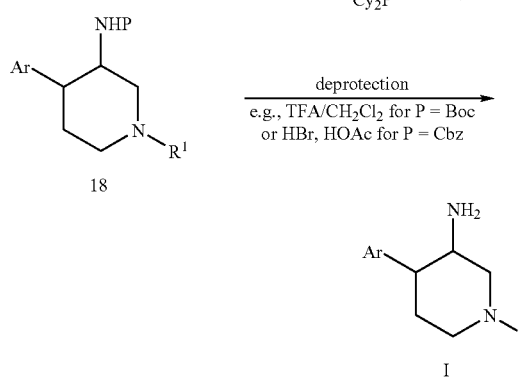

In some cases the product I or synthetic intermediates illustrated in the above schemes may be further modified, for example, by manipulation of substituents on Ar or $R^1$. These manipulations may include, but are not limited to, reduction, oxidation, alkylation, arylation, acylation, condensation, addition, cyclization, and hydrolysis reactions that are commonly known to those skilled in the art.

One such example is illustrated in Scheme 8. Intermediate 19 may be prepared by reaction of IIb and 2,4-dichloropyrimidine using thermal conditions described in Scheme 7. Further manipulation of intermediate 19 may be accomplished using a palladium-catalyzed Suzuki coupling of 19 with a boronic acid to provide intermediate 20. Deprotection of 20 may be accomplished, for example, by treatment with hydrogen gas and a catalyst such as palladium on carbon in a solvent such as methanol or ethyl acetate to provide compound I wherein $R^2$ is defined above.

SCHEME 8

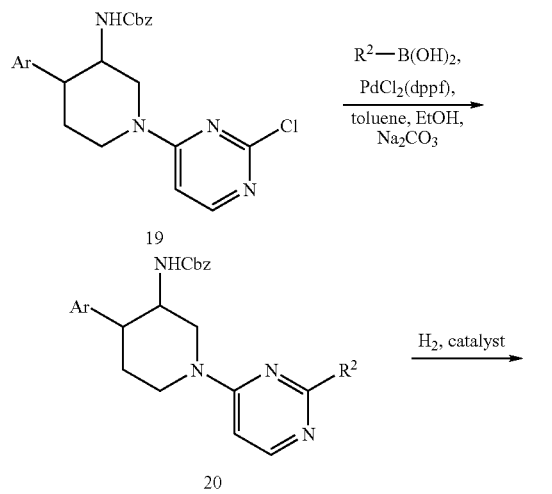

Another such example is illustrated in Scheme 9. Intermediate 22 may be prepared by reaction of 2,6-dichloro-3-nitropyridine with a primary amine such as methylamine in a solvent such as DMF with a base such as sodium carbonate. Chloride 22 may then be coupled with IIa using thermal conditions described in Scheme 7 to afford aminopyridine 23. Further manipulation of intermediate 23 may be accomplished by reduction of the nitro group with, for example, hydrogen gas and a Raney nickel catalyst to provide intermediate 24. Imidazole 25 may then be prepared by heating diamine 24 with an alkyl orthoformate such as trimethylorthoacetate. Deprotection of 25 may be accomplished, for example, by treatment with an acid such as trifluoroacetic acid or hydrochloric acid in a solvent such as methanol, ethyl acetate, or dichloromethane to provide compound I wherein $R^2$ is defined above.

SCHEME 9

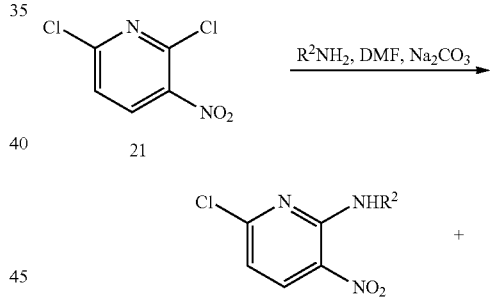

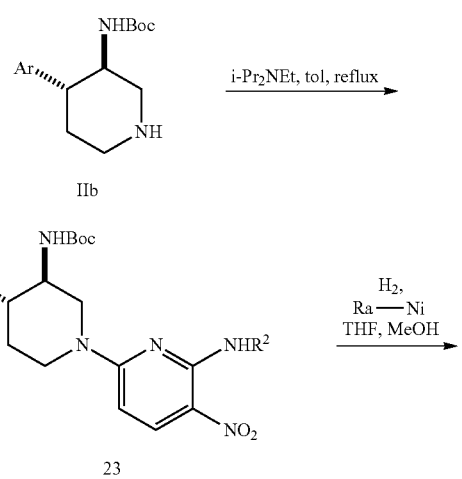

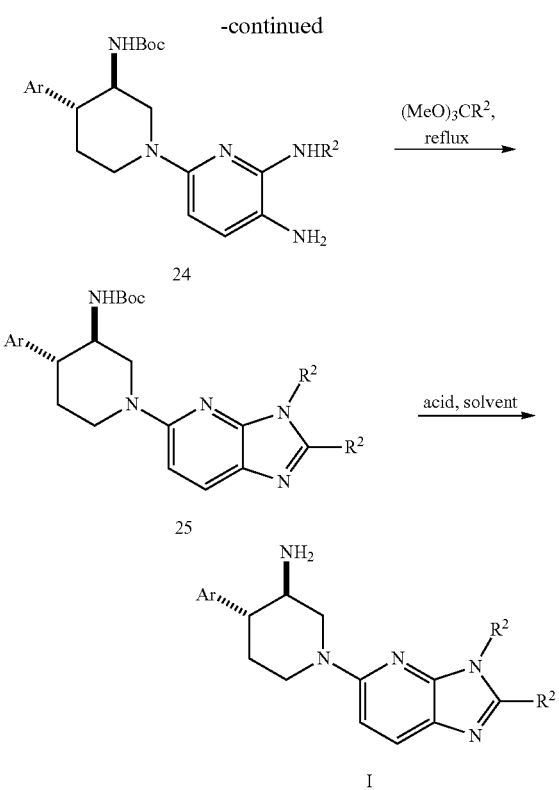

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate 1

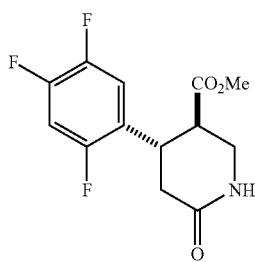

Methyl-trans-6-oxo-4-(2,4,5-trifluorophenyl)piperidine-3-carboxylate

Step A: Ethyl 3-(2,4,5-trifluorophenyl)acrylate

To a solution of 10 g (62 mmol) of 2,4,5-trifluorobenzaldehyde and 14 mL (70 mmol) of triethyl phosphonoacetate in 200 mL of tetrahydrofuran was added 11 mL (75 mmol) of 1,8-diazobicyclo[5.4.0]undec-7-ene. The solution was stirred at ambient temperature for 4 h then concentrated in vacuo and dissolved in 800 mL of a 10:1 solution of hexane/ethyl acetate. The resulting solution was washed sequentially with 1N hydrochloric acid, saturated aqueous sodium bicarbonate solution, and saturated aqueous brine (200 mL each). The organic phase was then dried over magnesium sulfate, filtered, and evaporated in vacuo to yield a crude oil. The crude material was then purified by flash chromatography on a Biotage Horizon® system (silica gel, 0 to 15% ethyl acetate/hexanes gradient) to give ethyl 3-(2,4,5-trifluorophenyl)acrylate as a colorless oil. $^1$H NMR (500 MHz, CDCl$_3$): δ 7.71 (d, J=16.2 Hz, 1H), 7.37 (ddd, J=17.1, 8.7, 1.8 Hz, 1H), 7.00 (ddd, J=16.2, 9.8, 2.4 Hz, 1H), 6.46 (d, J=16.2 Hz, 1H), 4.30 (q, J=7.1 Hz, 2H), 1.36 (t, J=7.1 Hz, 3H).

Step B: Dimethyl 2-cyano-3-(2,4,5-trifluorophenyl)pentanedioate

To a solution of 15 mL (64 mmol, 25% in methanol) of sodium methoxide in 200 mL of methanol was added 5.5 mL (62 mmol) of methyl cyanoacetate and the mixture was stirred at ambient temperature for 30 min. To this solution was added 14 g (62 mmol) of the product of Step A in 50 mL of methanol and the resulting yellow mixture was heated to reflux for 6 h. The mixture was then quenched carefully at ambient temperature with 1N aqueous hydrochloric acid (100 mL) and concentrated to remove methanol. The resulting mixture was extracted with three 300-mL portions of ethyl acetate, and the organic phases combined and washed sequentially with 1N hydrochloric acid, saturated aqueous sodium bicarbonate solution, and saturated aqueous brine (100 mL each). The organic phase was then dried over magnesium sulfate, filtered, and evaporated in vacuo to yield a viscous oil. The crude material was purified by flash chromatography on a Biotage Horizon® system (silica gel, 0 to 25% ethyl acetate/hexanes gradient) to give the title compound as a mixture of stereoisomers. $^1$H NMR (500 MHz, CDCl$_3$): δ 7.33-6.96 (m, 2H), 4.23-3.93 (series of m, 2H), 3.81-3.67 (series of s, 6H), 3.05-2.84 (m, 2H).

Step C: Methyl-trans-6-oxo-4-(2,4,5-trifluorophenyl)piperidine-3-carboxylate

To 450 mL of methanol at 0° C. was carefully added 30 mL of acetyl chloride and the resulting solution was allowed to stir at ambient temperature for 30 min. The resulting solution was added to 27 g (86 mmol) of dimethyl 2-cyano-3-(2,4,5-trifluorophenyl)pentanedioate from Step B and the reaction mixture was then shaken with 5.0 g of platinum (IV) oxide under 50 psi of hydrogen for 20 h. The mixture was filtered through a pad of Celite and the filter cake washed with methanol and dichloromethane. The combined filtrate and washings were concentrated and then taken up in 400 mL of 1:1 methanol/toluene with potassium carbonate (28 g, 200 mmol). The resulting mixture was heated to reflux for 4 h, then cooled to 0° C. and carefully quenched with 1N hydrochloric acid until the solution was acidic by pH paper. The resulting mixture was then extracted with six 300-mL portions of 3:1 chloroform/isopropyl alcohol and the organic phases combined and washed with saturated aqueous brine (300 mL). The organic phase was then dried over magnesium sulfate, filtered, and evaporated in vacuo to yield a colorless solid. This crude material was dissolved in 500 mL of 1:1 diethyl ether/methanol and cooled to 0° C. To this solution was added 75 mL (150 mmol) of trimethylsilyldiazomethane solution (2M in hexanes) in portions until a yellow color persisted. After warming to ambient temperature, the solution was stirred an additional 2 h, then concentrated in vacuo. The title compound was collected as a colorless crystalline solid which was used without further purification. LC/MS 288.3 (M+1).

Intermediate 2

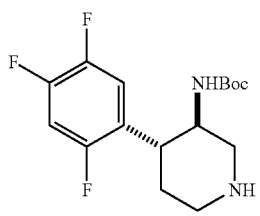

tert-Butyl [(3R,4R)-4-(2,4,5-trifluorophenyl)piperidin-3-yl]carbamate

Step A: Methyl trans-1-benzyl-6-oxo-4-(2,4,5-trifluorophenyl)piperidine-3-carboxylate To a stirred solution of 8.0 g (28 mmol) of Intermediate 1 in 150 mL of 5:1 tetrahydrofuran/N,N-dimethylformamide at −78° C. was added 32 mL (32 mmol) of sodium bis(trimethylsilyl)amide (1M in tetrahydrofuran) and the resulting solution was stirred at −78° C. for 20 min. Benzyl bromide (4.2 mL, 35 mmol) was then added and the resulting solution was stirred at 0° C. for 60 min, then allowed to warm to ambient temperature over 12 h. The mixture was quenched with 1N aqueous hydrochloric acid (100 mL) and concentrated to remove the tetrahydrofuran. The resulting mixture was extracted with three 300-mL portions of ethyl acetate, and the organic phases combined and washed sequentially with 1N hydrochloric acid, saturated aqueous sodium bicarbonate solution, and saturated aqueous brine (100 mL each). The organic phase was dried over magnesium sulfate, filtered, and evaporated in vacuo to yield a viscous oil. The crude material was purified by flash chromatography on a Biotage Horizon® system (silica gel, 0 to 50% ethyl acetate/hexanes gradient) to give methyl-trans-1-benzyl-6-oxo-4-(2,4,5-trifluorophenyl)piperidine-3-carboxylate. LC/MS 378.4 (M+1).

Step B: trans-1-Benzyl-6-oxo-4-(2,4,5-trifluorophenyl)piperidine-3-carboxylic acid To a solution of 8.4 g (22.2 mmol) of methyl-trans-1-benzyl-6-oxo-4-(2,4,5-trifluorophenyl)piperidine-3-carboxylate in 200 mL of 3:1 tetrahydrofuran/methanol was added 50 mL (50 mmol) of a 1N aqueous lithium hydroxide solution and the resulting mixture was stirred at 60° C. for 2 h. The solution was concentrated and acidified with 100 mL of 1N aqueous hydrochloric acid. The resulting mixture was then extracted with three 250-mL portions of ethyl acetate, and the organic phases combined and washed sequentially with 1N hydrochloric acid and saturated aqueous brine (200 mL each). The organic phase was dried over magnesium sulfate, filtered, and evaporated in vacuo to yield the title acid as a colorless foamy solid that was used without further purification. LC/MS 364.3 (M+1).

Step C: Methyl tert butyl [trans-1-benzyl-6-oxo-4-(2,4,5-trifluorophenyl)piperidin-3-yl]carbamate To 7.1 g (20 mmol) of the product of Step B in 150 mL of toluene was added 3.4 mL (24 mmol) of triethylamine followed by 4.7 mL (22 mmol) of diphenylphosphoryl azide. After stirring at ambient temperature for 30 min, the reaction mixture was warmed to 70° C. for 30 min, then slowly heated to reflux for an additional 2 h. The reaction mixture was cooled to ambient temperature, 6.3 g (59 mmol) of benzyl alcohol was added, and the reaction mixture was heated to reflux for 5 h. The solution was then cooled to ambient temperature and quenched with 1N aqueous hydrochloric acid (100 mL). The resulting mixture was extracted with four 200-mL portions of ethyl acetate, the organic phases combined and washed sequentially with 1N hydrochloric acid, saturated aqueous sodium bicarbonate solution, and saturated aqueous brine (100 mL each). The organic phase was then dried over magnesium sulfate, filtered, and evaporated in vacuo to yield a viscous crude oil which contained benzyl alcohol. This crude material was then dissolved in 150 mL of methanol with 3.3 g (15 mmol) of di-tert-butyldicarbonate and the solution was shaken with 1.0 g of palladium hydroxide (20% on carbon) under 45 psi of hydrogen for 12 h. The mixture was filtered through a pad of Celite and the filter cake washed with methanol and dichloromethane. The combined filtrate and washings were concentrated and purified by flash chromatography on a Biotage Horizon® system (silica gel, 0 to 60% ethyl acetate/hexanes gradient) to give the title compound as a colorless crystalline solid. LC/MS 435.5 (M+1).

Step D: tert-Butyl [(3S,4S)-1-benzyl-4-(2,4,5-trifluorophenyl)piperidin-3-yl]carbamate and tert-butyl [(3R,4R)-1-benzyl-4-(2,4,5-trifluorophenyl)piperidin-3-yl]carbamate To 6.6 g (15 mmol) of the product of Step C in 50 mL of tetrahydrofuran was added 45 mL (45 mmol) of borane (1M in THF) and the reaction mixture was heated to reflux for 3 h. The reaction mixture was then cooled to ambient temperature, 6N hydrochloric acid (50 mL) was added, and the resulting mixture was heated to reflux for an additional 2 h. The reaction mixture was then cooled to ambient temperature and quenched carefully with 2N aqueous sodium hydroxide (about 180 mL) until the solution was neutral by pH paper. Saturated aqueous sodium bicarbonate solution (100 mL) was then added to the solution followed by 100 mL of tetrahydrofuran and 5.5 g (25 mmol) of di-tert-butyldicarbonate. After stirring at ambient temperature for 10 h, the solution was concentrated, then extracted with three 150-mL portions of ethyl acetate. The organic phases were combined and washed sequentially with saturated aqueous sodium bicarbonate solution and saturated aqueous brine (100 mL each). The organic phase was then dried over magnesium sulfate, filtered, and evaporated in vacuo to yield a crude oil, which was purified by flash chromatography on a Biotage Horizon® system (silica gel, 0 to 40% ethyl acetate/hexanes gradient) to give the title compound as a colorless crystalline solid. Chiral HPLC separation (ChiralCel AD column, 5% isopropyl alcohol/heptane) gave the 3S, 4S enantiomer A as the more mobile eluting compound and the 3R, 4R enantiomer B, as the less mobile eluting compound. For A: LC/MS 421.5 (M+1). For B: LC/MS 421.5 (M+1).

Step E: tert-Butyl [(3R,4R)-4-(2,4,5-trifluorophenyl)piperidin-3-yl]carbamate

A solution of 2.3 g (5.5 mmol) of enantiomer B from Step D in 80 mL of methanol was stirred with 1.0 g of palladium hydroxide (20% on carbon) under 1 atmosphere of hydrogen at ambient temperature for 12 h. The mixture was filtered through a pad of Celite and the filter cake washed with methanol and dichloromethane. The combined filtrate and washings were concentrated and used without further purification to give Intermediate 2 as a colorless crystalline solid. LC/MS 331.3 (M+1).

Intermediate 3

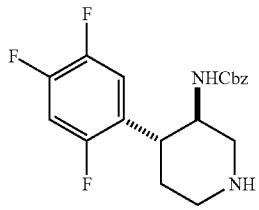

Benzyl [(3R,4R)-4-(2,4,5-trifluorophenyl)piperidin-3-yl]carbamate

Step A: Methyl (3R,4S)-6-methoxy-4-(2,4,5-trifluorophenyl)-2,3,4,5-tetrahydropyridine-3-carboxylate and methyl (3S,4R)-6-methoxy-4-(2,4,5-trifluorophenyl)-2,3,4,5-tetrahydropyridine-3-carboxylate To a stirred solution of 20 g (69 mmol) of Intermediate 1 in 200 mL of dichloromethane was added 13 g (85 mmol) of trimethyloxonium tetrafluoroborate and the resulting mixture was stirred at ambient temperature for 15 h. The mixture was next cooled to 0° C. and then quenched with saturated aqueous sodium bicarbonate solution (300 mL). The resulting mixture was extracted with three 300-mL portions of dichloromethane, and the organic phases combined and washed sequentially with saturated aqueous sodium bicarbonate solution and saturated aqueous brine (200 mL each). The organic phase was then dried over magnesium sulfate, filtered, and evaporated in vacuo. The crude crystalline solid was then purified by flash chromatography on a Biotage Horizon® system (silica gel, 20 to 100% ethyl acetate/hexanes gradient) to give methyl trans-6-methoxy-4-(2,4,5-trifluorophenyl)-2,3,4,5-tetrahydropyridine-3-carboxylate as a colorless crystalline solid along with recovered starting material. Chiral HPLC separation (ChiralCel AD column, 3% isopropyl alcohol/heptane) gave the 3R, 4S enantiomer A, as the more mobile eluting compound and the 3S, 4R enantiomer B as the less mobile eluting compound. For A: LC/MS 302.3 (M+1). For B: LC/MS 302.3 (M+1).

Step B: 1-tert-Butyl 3-methyl (3R,4S)-4-(2,4,5-trifluorophenyl)piperidine-1,3-dicarboxylate To 5.0 g (17 mmol) of enantiomer A of Step A in 200 mL of ethanol was added 5.0 g (132 mmol) of sodium borohydride and the resulting mixture was stirred at ambient temperature for 14 h. The reaction mixture was then quenched carefully with 3N aqueous phosphoric acid (50 mL). Potassium carbonate was then added until the solution was neutral by pH paper, then an additional 100 mL of saturated aqueous sodium bicarbonate solution was added with 200 mL of tetrahydrofuran and 6.5 g (30 mmol) of di-tert-butyldicarbonate. After stirring at ambient temperature for 6 h, the mixture was extracted with three 150-mL portions of ethyl acetate, and the organic phases combined and washed sequentially with 1N hydrochloric acid, saturated aqueous sodium bicarbonate solution, and saturated aqueous brine (100 mL each). The organic phase was then dried over magnesium sulfate, filtered, and evaporated in vacuo to yield a viscous oil. This crude material was then purified by flash chromatography on a Biotage Horizon® system (silica gel, 0 to 40% ethyl acetate/hexanes gradient) to give the title compound as a colorless oil. LC/MS 396.3 (M+23).

Step C: (3R,4S)-1-(tert-Butoxycarbonyl)-4-(2,4,5-trifluorophenyl)piperidine-3-carboxylic Acid To 3.3 g (15 mmol) of the product of Step B in 200 mL of 3:1 tetrahydrofuran/methanol was added 50 mL (50 mmol) of 1N aqueous lithium hydroxide solution and the resulting solution was stirred at ambient temperature for 16 h, then concentrated and acidified with 100 mL of 1N aqueous hydrochloric acid. The resulting mixture was extracted with three 100-mL portions of ethyl acetate, and the organic phases combined and washed sequentially with 1N hydrochloric acid and saturated aqueous brine (100 mL each). The organic phase was dried over magnesium sulfate, filtered, and evaporated in vacuo to yield the title compound as a colorless foamy solid that was used without further purification. LC/MS 382.4 (M+23).

Step D: tert-Butyl (3R,4R)-3-{[(benzyloxy)carbonyl]amino}-4-(2,4,5-trifluorophenyl)piperidine-1-carboxylate To 2.8 g (7.8 mmol) of the product of Step C in 50 mL of toluene was added 1.3 mL (9.0 mmol) of triethylamine followed by 1.9 mL (9.0 mmol) of diphenylphosphoryl azide. After stirring at ambient temperature for 30 min, the reaction mixture was warmed to 70° C. for 30 min then slowly heated to reflux for an additional 2 h. The reaction mixture was then cooled to ambient temperature and 2.4 mL (22 mmol) of benzyl alcohol was added. The reaction mixture was heated to reflux for 5 h then cooled to ambient temperature and quenched with 1N aqueous hydrochloric acid (100 mL). The resulting mixture was extracted with three 150-mL portions of ethyl acetate, and the organic phases combined and washed sequentially with 1N hydrochloric acid, saturated aqueous sodium bicarbonate solution, and saturated aqueous brine (70 mL each). The organic phase was then dried over magnesium sulfate, filtered, and evaporated in vacuo to yield a viscous crude oil which was purified by flash chromatography on a Biotage Horizon® system (silica gel, 0 to 30% ethyl acetate/hexanes gradient) to give the title compound as a viscous oil. LC/MS 365.3 (M-Boc).

Step E: Benzyl [(3R,4R)-4-(2,4,5-trifluorophenyl)piperidin-3-yl]carbamate

The product from Step D was dissolved into 40 ml of 1:1 dichloromethane/trifluoroacetic acid and stirred at ambient temperature for 60 min. The solution was then concentrated and taken up in 250 mL of 3:1 chloroform/isopropyl alcohol then washed with saturated aqueous sodium bicarbonate solution, and saturated aqueous brine (100 mL each). The organic phase was then dried over magnesium sulfate, filtered, and evaporated in vacuo to yield the title compound as a colorless crystalline solid which was used without further purification. LC/MS 365.4 (M+1).

Intermediate 4

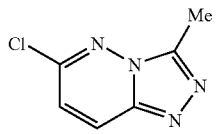

6-Chloro-3-methyl[1,2,4]triazolo[4,3-b]pyridazine

To a stirred solution of 1.0 g (6.7 mmol) of 3,6-dichloropyridazine in 5 mL of butanol was added 500 mg (6.7 mmol) of acetic hydrazide and the resulting solution was stirred under nitrogen at reflux for 24 h. The reaction mixture was then cooled to ambient temperature, filtered, and the resulting precipitate washed with ethyl acetate and methanol. The combined filtrate and washings were concentrated and dissolved in 250 mL of 10:1 chloroform/methanol then washed with saturated aqueous brine (2×100 mL). The organic phase was then dried over magnesium sulfate, filtered, and evaporated in vacuo to yield a yellow solid. The crude material was purified by flash chromatography on a Biotage Horizon® system (silica gel, 0 to 80% ethyl acetate/hexanes gradient) to give the title compound as a brown crystalline solid. LC/MS 169.0 (M+1).

Intermediate 5

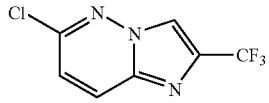

6-Chloro-2-(trifluoromethyl)imidazo[1,2-b]pyridazine

Intermediate 5 may be prepared using a similar route described in the literature (C. Enguehard, et. al. *Synthesis*, 2001, 4, 595-600). A solution of 1.0 g (7.7 mmol) of 6-chloropyridazin-3-amine and 1.0 mL (10 mmol) 3-bromo-1,1,1-trifluoroacetone in 10 mL ethanol was heated to reflux for 5 h. The resulting mixture was cooled to ambient temperature and evaporated in vacuo to yield a viscous oil which was then taken up in saturated aqueous sodium carbonate until the solution was basic by pH paper. The aqueous phase was extracted with three 50 mL portions of dichloromethane, and the organic phases then combined, dried over magnesium sulfate, filtered and evaporated in vacuo to yield a yellow solid. The crude material was purified by flash chromatography on a Biotage Horizon® system (silica gel, 0 to 40% ethyl acetate/hexanes gradient) to give Intermediate 5 as a yellow crystalline solid. LC/MS 222.3 (M+1).

Intermediate 6

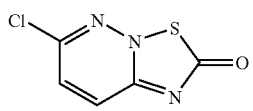

6-Chloro-2H-[1,2,4]thiadiazolo[2,3-b]pyridazin-2-one

Intermediate 6 was prepared using a synthetic route described in the literature (K. Pilgram, et. al. *J. Org. Chem.* 1973, 38, 1575-1578). LC/MS 188.1 (M+1).

Intermediate 7

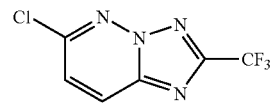

6-Chloro-2-(trifluoromethyl)[1,2,4]triazolo[1,5-b]pyridazine

Step A: N-(6-Chloropyridazin-3-yl)-2,2,2-trifluoroacetamide

To a solution of 2 g (15 mmol) of 6-chloropyridazin-3-amine and 2.4 mL (17 mmol) of triethylamine in 150 mL dichloromethane at 0° C. was carefully added 2.1 mL (15 mmol) trifluoroacetic acid anhydride. The resulting solution was allowed to warm to ambient temperature then concentrated in vacuo and dissolved in 200 mL of a 3:1 solution of chloroform/isopropanol. The resulting solution was washed sequentially with saturated aqueous sodium bicarbonate solution and saturated aqueous brine (200 mL each). The organic phase was then dried over magnesium sulfate, filtered, and evaporated in vacuo to yield a crude oil which was carried forward without purification.

Step B: (1Z)-N-(6-Chloropyridazin-3-yl)-2,2,2-trifluoroethanimidoyl chloride A solution of 3.8 g (17 mmol) of the crude product of Step A and 4.2 g (22 mmol) of phosphorous pentachloride in 200 mL of dichloroethane was heated at reflux temperature under nitrogen. After 6 h the reaction was cooled to ambient temperature then concentrated in vacuo to yield a crude oil which was carried on to Step C.

Step C: (1Z)-N-(6-Chloropyridazin-3-yl)-2,2,2-trifluoro-N'-hydroxyethanimidamide To a solution of 4.5 g (18 mmol) of the crude product of Step B in 150 mL tetrahydrofuran was carefully added 2 mL aqueous 50% methoxyamine. The resulting solution was stirred under nitrogen at ambient temperature. After 1 h the solution was concentrated in vacuo then dissolved in 100 mL ethyl acetate and washed sequentially with saturated sodium bicarbonate solution and saturated aqueous brine (100 mL each). The organic phase was then dried over magnesium sulfate, filtered, and evaporated in vacuo to yield a crude oil.

Step D: 6-Chloro-2-(trifluoromethyl)[1,2,4]triazolo[1,5-b]pyridazine

To 2.2 g (9.0 mmol) crude product of Step C was added 2 mL concentrated polyphosphoric acid and the resulting mixture was stirred under nitrogen at 150° C. for 4 h. The reaction mixture was then cooled to 0° C. and quenched carefully with concentrated ammonium hydroxide until the solution was basic by pH paper. The resulting solution was then extracted with three 100 mL portions of ethyl acetate, and the organic phases combined and washed with 250 mL saturated aqueous brine. The organic phase was then dried over magnesium sulfate, filtered, and evaporated in vacuo to yield a crude oil. The crude material was purified by flash chromatography on a Biotage Horizon® system (silica gel, 0 to 80% ethyl acetate/hexanes gradient) to give Intermediate 7 as a yellow crystalline solid. LC/MS 223.2 (M+1).

Intermediate 8

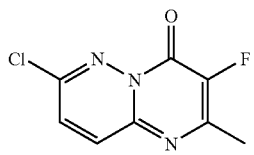

7-Chloro-2-fluoro-3-methyl-4H-pyrimido[1,2-b]pyridazin-4-one

Intermediate 8 may be prepared using a variation of a route described in the literature (C. Avellana, et. al. *J. Heterocyclic Chem.*, 1977, 14, 325-327). To a stirred solution of 1.0 g (7.7 mmol) of 6-chloropyridazin-3-amine in 5 mL benzyl alcohol was added 1.4 mL (11.6 mmol) ethyl 2-fluoroacetoacetate. The resulting solution was refluxed for 24 h then evaporated in vacuo to yield a crude solid which was purified by flash chromatography on a Biotage Horizon® system (silica gel, 0 to 80% ethyl acetate/hexanes gradient) to give Intermediate 8 as a brown crystalline solid. LC/MS 214.2 (M+1).

Intermediate 9

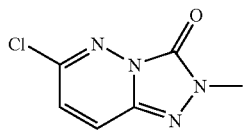

6-Chloro-2-methyl[1,2,4]triazolo[4,3-b]pyridazin-3(2H)-one

Step A: 6-Chloro[1,2,4]triazolo[4,3-b]pyridazin-3(2H)-one

To a stirring solution of 3 g (20 mmol) of 3,6-dichloropyridazine and 4.5 g (40 mmol) semicarbazide hydrochloride in 100 mL of a 3:1 mixture of ethanol/water was added 5 drops of concentrated hydrochloric acid. The resulting solution was heated to reflux for 24 h under nitrogen then evaporated in vacuo and the resulting solid was recrystallized from ethanol to yield the title compound as a yellow crystalline solid. A similar route to this compound is described in the literature (P. Francavilla, et. al. *J. Heterocyclic Chem.*, 1971, 8, 415-419). LC/MS 171.2 (M+1).

Step B: 6-Chloro-2-methyl[1,2,4]triazolo[4,3-b]pyridazin-3(2H)-one

To a stirred solution of 150 mg (0.88 mmol) of the product of Step A in 10 mL of 5:1 tetrahydrofuran/N,N-dimethylformamide at −78° C. was added 0.88 mL (0.88 mmol) of sodium bis(trimethylsilyl)amide (1M in tetrahydrofuran) and the resulting solution was stirred at −78° C. for 30 min. Methyl iodide (0.120 mL, 1.9 mmol) was then added and the resulting solution was stirred at 0° C. for 1 h, then allowed to warm to ambient temperature over 24 h. The resulting mixture was extracted with three 20 mL portions of ethyl acetate, and the organic phases combined and washed sequentially with 1N hydrochloric acid, saturated aqueous sodium bicarbonate solution, and saturated aqueous brine (75 mL each). The organic phase was dried over magnesium sulfate, filtered, and evaporated in vacuo to yield a viscous oil. The crude material was purified by flash chromatography on a Biotage Horizon® system (silica gel, 0 to 80% ethyl acetate/hexanes gradient) to give Intermediate 9. LC/MS 184.6 (M+1).

Intermediate 10

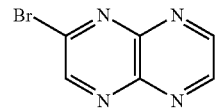

2-Bromopyrazino[2,3-b]pyrazine

To a stirred solution of 50 mg (0.27 mmol) of 5-bromopyrazine-2,3-diamine in 2 mL of a 10:1 solution of methanol/acetic acid was added 0.046 mL (0.40 mmol) of glyoxal solution (40 wt. % in water) and the resulting solution was stirred at 50° C. for 4 h. The reaction mixture was cooled to ambient temperature, diluted with 10 mL of ethyl acetate and washed with saturated aqueous sodium bicarbonate solution, and saturated aqueous brine (5 mL each). The organic phase was then dried over anhydrous sodium sulfate, filtered, and evaporated in vacuo to yield the title compound as a tan crystalline solid which was used without further purification. LC/MS 211.1, 213.1 (M+1, M+3).

Example 1

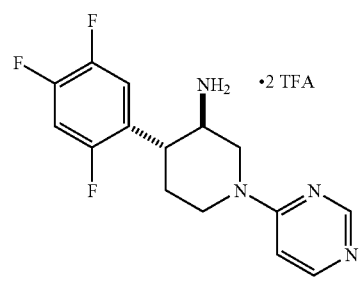

(3R,4R)-1-Pyrimidin-4-yl-4-(2,4,5-trifluorophenyl)piperidin-3-amine bis-trifluoroacetic acid salt Step A: Benzyl [(3R,4R)-1-(6-chloropyrimidin-4-yl)-4-(2,4,5-trifluorophenyl)piperidin-3-yl]carbamate A solution of 50 mg (0.14 mmol) of Intermediate 3 and 100 mg (0.67 mmol) of 4,6-dichloropyrimidine in 6 mL of 5:1 toluene/N,N-dimethylformamide was heated at reflux temperature under nitrogen. After 48 h the reaction was cooled to ambient temperature and subsequently diluted with 10 mL of ethyl acetate. The solution was then washed with saturated sodium bicarbonate solution and saturated aqueous brine (10 mL each). The organic phase was then dried over magnesium sulfate, filtered, and evaporated in vacuo to yield a crude oil, which was purified by reverse phase HPLC (YMC Pro-C18 column, gradient elution, 10 to 90% acetonitrile/water with 0.1% TFA) to afford the title compound as a colorless crystalline solid. LC/MS 477.3 (M+1).

Step B: (3R,4R)-1-Pyrimidin-4-yl-4-(2,4,5-trifluorophenyl)piperidin-3-amine bis-trifluoroacetic acid salt To 40 mg (0.084 mmol) of the product of Step A in 4 mL of 3:1 ethyl acetate/methanol was added 50 mg of 10% palladium on carbon. After stirring at ambient temperature for 4 h under 1 atmosphere of hydrogen, the reaction was filtered through a pad of Celite and the filter cake washed with dichloromethane. The combined filtrate and washings were concentrated and the crude material was purified by reverse phase HPLC (YMC Pro-C18 column, gradient elution, 0 to 80% acetonitrile/water with 0.1% TFA) to afford the title compound as a colorless crystalline solid. LC/MS 309.3 (M+1).

Example 2

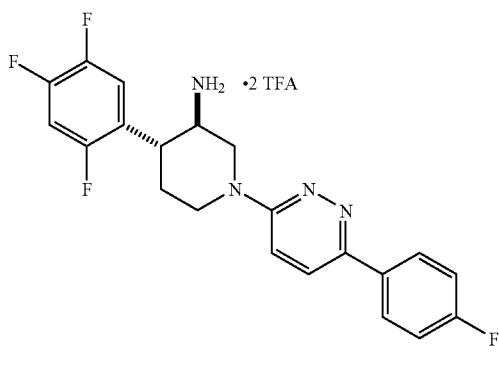

(3R,4R)-1-[6-(4-fluorophenyl)pyridazin-3-yl]-4-(2,4,5-trifluorophenyl)piperidin-3-amine bis-trifluoroacetic acid salt Step A: Benzyl [(3R,4R)-1-(6-chloropyridazin-3-yl)-4-(2,4,5-trifluorophenyl)piperidin-3-yl]carbamate A solution of 120 mg (0.33 mmol) of Intermediate 3 and 180 mg (1.2 mmol) of 3,6-dichloropyridazine in 6 mL of 5:1 toluene/N,N-dimethylformamide was heated at reflux temperature under nitrogen. After 24 h the reaction was cooled to ambient temperature and subsequently diluted with 10 mL of ethyl acetate. The solution was then washed with saturated sodium bicarbonate solution and saturated aqueous brine (10 mL each). The organic phase was then dried over magnesium sulfate, filtered, and evaporated in vacuo to yield a crude oil, which was purified by reverse phase HPLC (YMC Pro-C18 column, gradient elution, 10 to 90% acetonitrile/water with 0.1% TFA) to afford the title compound as a colorless crystalline solid. LC/MS 477.2 (M+1).

Step B: Benzyl [(3R,4R)-1-[6-(4-fluorophenyl)pyridazin-3-yl]-4-(2,4,5-trifluorophenyl)piperidin-3-yl] carbamate To a solution of 58 mg (0.12 mmol) of the product of Step A and 27 mg (0.19 mmol) of 4-fluorophenylboronic acid in 4 mL of 1:1 ethanol/toluene was added 0.60 mL (1.2 mmol) 2N aqueous sodium carbonate solution followed by 200 mg (0.245 mmol) of [1,1'-bis(diphenylphosphino)-ferrocene] dichloropalladium (II). The resulting solution was stirred under nitrogen at 100° C. for 24 h, then allowed to cool to ambient temperature. The reaction mixture was then filtered through a pad of Celite and the filter cake washed with ethyl acetate and methanol. The combined filtrate and washings were concentrated and the crude material was purified by reverse phase HPLC (YMC Pro-C18 column, gradient elution, 10 to 90% acetonitrile/water with 0.1% TFA) to afford the title compound as a yellow oil. LC/MS 537.3 (M+1).

Step C: (3R,4R)-1-[6-(4-fluorophenyl)pyridazin-3-yl]-4-(2,4,5-trifluorophenyl)piperidin-3-amine bis-trifluoroacetic acid salt To 38 mg (0.071 mmol) of the product of Step B was added 3 mL of 30% hydrogen bromide in acetic acid, and the solution was allowed to stir at ambient temperature for 1 h. The resulting solution was then evaporated in vacuo to yield a viscous crude oil which was purified by reverse phase HPLC (YMC Pro-C18 column, gradient elution, 0 to 80% acetonitrile/water with 0.1% TFA) to afford the title compound as a colorless crystalline solid. LC/MS 403.2 (M+1).

Example 3

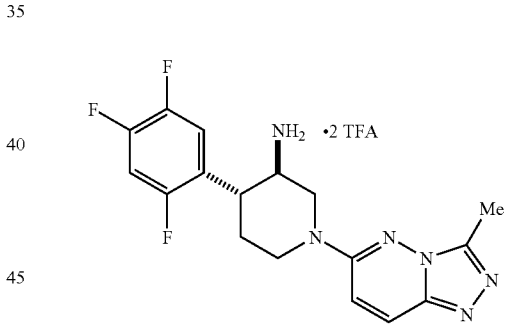

(3R,4R)-1-(3-Methyl[1,2,4]triazolo[4,3-b]pyridazin-6-yl)-4-(2,4,5-trifluorophenyl)piperidin-3-amine bis-trifluoroacetic acid salt Step A: tert-Butyl [(3R,4R)-1-(3-methyl[1,2,4]triazolo[4,3-b]pyridazin-6-yl)-4-(2,4,5-trifluorophenyl)piperidin-3-yl]carbamate To a solution of 50 mg (0.15 mmol) of Intermediate 2 and 64 mg (0.38 mmol) of Intermediate 4 in 2 mL toluene was added 0.032 mL (0.23 mmol) of triethylamine and the resulting solution was heated at reflux temperature under nitrogen. After 24 h the reaction was cooled to ambient temperature and subsequently diluted with 10 mL of ethyl acetate. The solution was then washed with saturated sodium bicarbonate solution and saturated aqueous brine (10 mL each). The organic phase was then dried over magnesium sulfate, filtered, and evaporated in vacuo to yield a crude oil, which was purified by reverse phase HPLC (YMC Pro-C18 column, gradient elution, 10 to 90% acetonitrile/water with 0.1% TPA) to afford the title compound as a colorless crystalline solid. LC/MS 463.4 (M+1).

Step B: (3R,4R)-1-(3-Methyl[1,2,4]triazolo[4,3-b] pyridazin-6-yl)-4-(2,4,5-trifluorophenyl)piperidin-3-amine bis-trifluoroacetic acid salt The product from Step A (24 mg, 0.067 mmol) was dissolved in 10 mL of 1:1 dichloromethane/trifluoroacetic acid and stirred at ambient temperature for 60 min. The solution was then concentrated to yield a viscous crude oil which was purified by reverse phase HPLC (YMC Pro-C18 column, gradient elution, 0 to 80% acetonitrile/water with 0.1% TFA) to afford the title compound as a colorless crystalline solid. LC/MS 363.4 (M+1).

Example 4

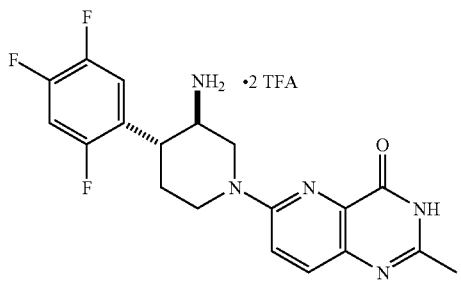

6-[(3R,4R)-3-Amino-4-(2,4,5-trifluorophenyl)piperidin-1-yl]-2-methylpyrido[3,2-d]pyrimidin-4(3H)-one bis-trifluoroacetic acid salt Step A: tert-Butyl[(3R,4R)-1-[6-(aminocarbonyl)-5-nitropyridin-2-yl]-4-(2,4,5-trifluorophenyl)piperidin-3-yl]carbamate To a solution of 700 mg (2.1 mmol) of Intermediate 2 and 770 mg (4.2 mmol) of 6-chloro-3-nitropyridine-2-carboxamide (prepared as in G. W. Rewcastle, et. al. *J. Med. Chem.* 1996, 39, 1823-1835) in 8 mL of toluene and 4 mL of N,N-dimethylformamide was added 1.7 mL (10.6 mmol) of N,N-diisopropylethylamine and the solution was stirred under nitrogen at reflux for 30 h. The reaction mixture was then cooled to ambient temperature, diluted with 15 mL of methylene chloride and poured into 100 mL of a saturated aqueous bicarbonate solution. The layers were separated and the aqueous layer extracted with three 100 mL portions of methylene chloride and the combined organic phases were dried over anhydrous magnesium sulfate, filtered and evaporated in vacuo to yield a yellow solid. The yellow solid was purified by flash chromatography on a Biotage Horizon® system (silica gel, 0 to 70% ethyl acetate/hexanes gradient) to give the title compound as a yellow crystalline solid. LC/MS 496.6 (M+1).

Step B: tert-Butyl[(3R,4R)-1-[5-amino-6-(aminocarbonyl)pyridin-2-yl]-4-(2,4,5-trifluorophenyl)piperidin-3-yl]carbamate To 993 mg (2.0 mmol) of the product of Step A in 40 mL of 3:1 methanol/tetrahydrofuran at 0° C. was added 166 mg (0.70 mmol) of nickel (II) chloride hexahydrate followed by 318 mg (8.4 mmol) of sodium borohydride in portions over 30 min. The reaction mixture was stirred for an additional 30 min and then quenched with 100 mL of a saturated aqueous sodium bicarbonate solution. The layers were separated and the aqueous phase extracted with three 100-mL portions of 3:1 chloroform/isopropyl alcohol. The combined organic phases were dried over anhydrous magnesium sulfate, filtered and evaporated in vacuo to yield a yellow solid which was purified by flash chromatography on a Biotage Horizon® system (silica gel, 0 to 100% ethyl acetate/hexanes gradient) to give the title compound as a yellow crystalline solid. LC/MS 465.6 (M+1).

Step C: tert-Butyl[(3R,4R)-1-1(2-methyl-4-oxo-3,4-dihydropyrido[3,2-d]pyrimidine-6-yl)-4-(2,4,5-trifluorophenyl)piperidin-3-yl]carbamate To 20 mg (0.04 mmol) of the product from Step B in 1 mL of toluene was added 0.08 mL (0.4 mmol) triethyl orthoacetate and the resulting solution was stirred under nitrogen at reflux for 48 h. The reaction mixture was then cooled to ambient temperature and diluted with 10 mL of a 1:1 solution of methylene chloride/saturated aqueous sodium bicarbonate solution. The layers were separated and the aqueous layer extracted with three 5-mL portions of methylene chloride, and the organic phases combined and dried over anhydrous sodium sulfate, filtered and concentrated in vacuo to yield a viscous crude oil. The crude oil was purified by preparative thin layer chromatography using an Analtech® 1000 micron plate (ethyl acetate solvent) to give the title compound as a viscous oil. LC/MS 490.1 (M+1).

Step D: 6-[(3R,4R)-3-Amino-4-(2,4,5-trifluorophenyl)piperidin-1-yl]-2-methylpyrido[3,2-d]pyrimidin-4(3H)-one bis-trifluoroacetic acid salt T/he product from Step C (10 mg, 0.02 mmol) was dissolved in 4 mL of 1:1 dichloromethane/trifluoroacetic acid and stirred at ambient temperature for 60 min. The solution was then concentrated to yield a viscous crude oil which was purified by reverse phase HPLC (YMC Pro-C18 column, gradient elution, 0 to 80% acetonitrile/water with 0.1% TFA) to afford the title compound as a colorless crystalline solid. LC/MS 390.1 (M+1).

Example 5

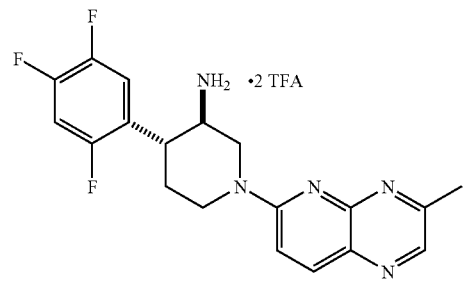

(3R,4R)-1-3-(3-Methylpyrido[2,3-b]pyrazin-6-yl)-4-(2,4,5-trifluorophenyl)piperidin-3-amine bis-trifluoroacetic acid salt Step A: tert-Butyl [(3R,4R)-1-(6-amino-5-nitropyridin-2-yl)-4-(2,4,5-trifluorophenyl)piperidin-3-yl] carbamate To a solution of 200 mg (0.6 mmol) of Intermediate 2 and 115 mg (0.66 mmol) of 6-chloro-3-nitropyridin-2-amine in 8 mL of toluene was added 0.21 mL (1.2 mmol) of N,N-diisopropylethylamine and the solution was stirred under nitrogen at reflux for 5 h. The reaction mixture was then cooled to ambient temperature, diluted with 15 mL of methylene chloride and poured into 15 mL of a saturated aqueous bicarbonate solution. The layers were separated and the aqueous layer extracted with three 15 mL portions of methylene chloride and the combined organic phases were dried over anhydrous sodium sulfate, filtered and evaporated in vacuo to yield a yellow solid. The yellow solid was purified by flash chromatography on a Biotage Horizon® system (silica gel, 0 to 60% ethyl acetate/hexanes gradient) to give the title compound as a yellow crystalline solid. LC/MS 468.2 (M+1).

Step B: tert-Butyl [(3R,4R)-1-(5,6-diaminopyridin-2-yl)-4-(2,4,5-trifluorophenyl)piperidin-3-yl]carbamate To 85 mg (0.18 mmol) of the product of Step A in 4 mL of 3:1 methanol/tetrahydrofuran at 0° C. was added 2.5 mg (0.01 mmol) of nickel (II) chloride hexahydrate followed by 40 mg (1.0 mmol) of sodium borohydride in four 10 mg portions every 5 min. The reaction mixture was stirred for an additional 10 min and poured into 20 mL of a 1:1 mixture of methylene chloride/saturated aqueous ammonium chloride solution. The layers were separated and the aqueous phase extracted with three 10-mL portions of methylene chloride. The combined organic phases were dried over anhydrous sodium sulfate, filtered and evaporated in vacuo to yield a purple solid which was purified by preparative thin layer chromatography using an Analtech® 1500 micron plate (1:2 hexane/ethyl acetate solvent) to give the title compound as a purple crystalline solid. LC/MS 438.1 (M+1).

Step C: tert-Butyl [(3R,4R)-1-(3-methylpyrido[2,3-b]pyrazin-6-yl)-4-(2,4,5-trifluorophenyl)piperidin-3-yl]carbamate To 40 mg (0.09 mmol) of the product of Step B in 2 mL of methanol was added 0.07 mL (0.46 mmol) of 2-oxopropanal solution (40 wt. % in water) and stirred at ambient temperature for 1 h. The reaction mixture was then, diluted with 10 mL of methylene chloride and poured into 10 mL of a saturated aqueous bicarbonate solution. The layers were separated and the aqueous layer extracted with three 10 mL portions of methylene chloride and the combined organic phases were dried over anhydrous sodium sulfate, filtered and evaporated in vacuo to yield a tan solid which was purified by preparative thin layer chromatography using an Analtech® 1500 micron plate (1:3 hexane/ethyl acetate solvent) to give the title compound as a tan crystalline solid. LC/MS 474.1 (M+1).

Step D: (3R,4R)-1-3-(3-Methylpyrido[2,3-b]pyrazin-6yl)-4-(2,4,5-trifluorophenyl)piperidin-3-amine bis-trifluoroacetic acid salt The product from Step C (5 mg, 0.01 mmol) was dissolved in 4 mL of 1:1 dichloromethane/trifluoroacetic acid and stirred at ambient temperature for 60 min. The solution was then concentrated to yield a viscous crude oil which was purified by reverse phase HPLC (YMC Pro-C18 column, gradient elution, 0 to 80% acetonitrile/water with 0.1% TFA) to afford the title compound as a colorless crystalline solid. LC/MS 374.1 (M+1).

Example 6

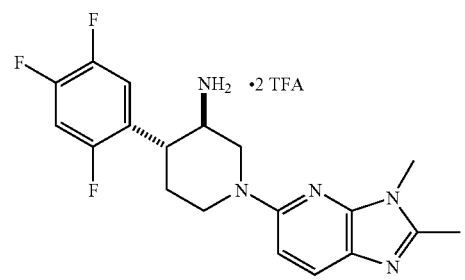

(3R,4R)-1-(2,3-Dimethyl-3H-imidazo[4,5-b]pyridin-5-yl)-4-(2,4,5-trifluorophenyl)piperidin-3-amine bis-trifluoroacetic acid salt

Step A: 6-Chloro-N-methyl-3-nitropyridin-2-amine

To a stirred solution of 10 g (52 mmol) of 2,6-dichloro-3-nitropyridine in 300 mL of N,N-dimethylformamide was added 26 mL (52 mmol) of methylamine (2M in tetrahydrofuran) and 9.3 g (88 mmol) of sodium carbonate and the resulting mixture was stirred for 24 h. The solution was diluted with 500 mL water and extracted with three 700 mL portions of ethyl acetate. The organic phase was dried over magnesium sulfate, filtered, and evaporated in vacuo to yield a viscous oil. The crude material was purified by flash chromatography on a Biotage Horizon® system (silica gel, 0 to 10% ethyl acetate/hexanes gradient) to give 6-chloro-N-methyl-3-nitropyridin-2-amine as a yellow solid. LC/MS 188.1 (M+1).

Step B: tert-Butyl[(3R,4R)-1-[6-(methylamino)-5-nitropyridin-2-yl]-4-(2,4,5-trifluorophenyl)piperidin-3-yl]carbamate To a solution of 300 mg (0.9 mmol) of Intermediate 2 and 206 mg (1.1 mmol) 6-chloro-N-methyl-3-nitropyridin-2-amine in 5 mL toluene was added 0.33 mL (1.4 mmol) of N,N-diisopropylethylamine and the solution was stirred under nitrogen at reflux for 24 h. The reaction mixture was then cooled to ambient temperature, diluted with 25 mL ethyl acetate, and washed sequentially with saturated aqueous sodium bicarbonate solution and saturated aqueous brine (25 mL each). The organic phase was then dried over magnesium sulfate, filtered, and evaporated in vacuo to yield a yellow solid which was purified by reverse phase HPLC (YMC Pro-C18 column, gradient elution, 10-90% acetonitrile/water with 0.1% trifluoroacetic acid) to afford the title compound as a yellow crystalline solid.

Step C: tert-Butyl[(3R,4R)-1-[5-amino-6-(methylamino)pyridine-2-yl]-4-(2,4,5-trifluorophenyl)piperidin-3-yl]carbamate To a stirring solution of 68 mg (0.14 mmol) of the product of Step B in 8 mL of 10:1 tetrahydrofuran/methanol under nitrogen was added 0.20 mL Raney Nickel (slurry in water).

The resulting mixture under hydrogen was heated at 40° C. for 1 h and then cooled to ambient temperature over 24 h. The mixture was then filtered through a pad of Celite and the filter cake washed with dichloromethane and methanol. The combined filtrate and washings were concentrated in vacuo and the resulting purple solid was purified by reverse phase HPLC (YMC Pro-C18 column, gradient elution, 10-90% acetonitrile/water with 0.1% trifluoroacetic acid) to afford the title compound as a purple crystalline solid. LC/MS 452.5 (M+1).

Step D: tert-Butyl[(3R,4R)-1-(2,3-dimethyl-3H-imidazo[4,5-b]pyridine-5-yl)-4-(2,4,5-trifluorophenyl)piperidin-3-yl]carbamate A solution of 114 mg (0.25 mmol) of the product of Step C in 5 mL of 1:1 trimethyl orthoacetate/toluene was heated at reflux under nitrogen for 24 h. The solution was cooled to ambient temperature then evaporated in vacuo and the crude oil was carried forward without further purification.

Step E: (3R,4R)-1-(2,3-dimethyl-3H-imidazo[4,5-b]pyridin-5-yl)-4-(2,4,5-trifluorophenyl)piperidin-3-amine bis-trifluoroacetic acid salt The crude product from Step D was dissolved in 5 mL of 1:1 dichloromethane/trifluoroacetic acid and stirred at ambient temperature for 60 min. The solution was then concentrated to yield a viscous crude oil which was purified by reverse phase HPLC (YMC Pro-C18 column, gradient elution, 0 to 80% acetonitrile/water with 0.1% TFA) to afford the title compound as a white crystalline solid. LC/MS 376.2 (M+1).

Following essentially the procedures outlined for Examples 1-6, the Examples listed in Table 1 were prepared.

TABLE 1

| Example | R¹ | MS (M + 1) |
|---|---|---|
| 7 | 2-pyridyl | 308.3 |
| 8 | 3-pyridyl | 308.4 |
| 9 | 4-pyridyl | 308.4 |

TABLE 1-continued

| Example | R¹ | MS (M + 1) |
|---|---|---|
| 10 | pyridazinyl | 309.3 |
| 11 | 2-pyrimidinyl | 309.3 |
| 12 | pyrazinyl | 309.3 |
| 13 | 6-chloro-2-pyridyl | 342.3 |
| 14 | 6-methoxy-2-pyridyl | 338.1 |
| 15 | 6-trifluoromethyl-2-pyridyl | 376.3 |
| 16 | 5-trifluoromethyl-2-pyridyl | 376.3 |
| 17 | 5-nitro-2-pyridyl | 353.3 |
| 18 | 5-cyano-2-pyridyl | 333.4 |

TABLE 1-continued
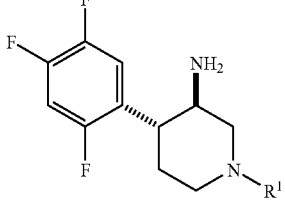
| Example | R¹ | MS (M + 1) |
|---|---|---|
| 19 | 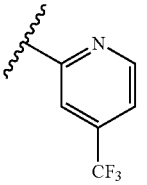 | 376.4 |
| 20 | 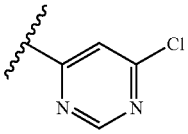 | 376.2 |
| 21 | 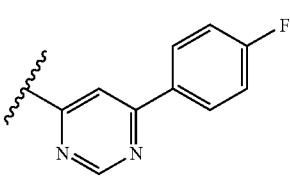 | 343.2 |
| 22 |  | 403.2 |
| 23 | 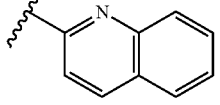 | 403.3 |
| 24 | 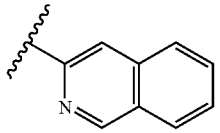 | 358.2 |
| 25 | 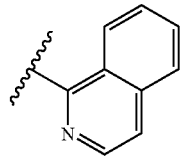 | 358.4 |
| 26 | 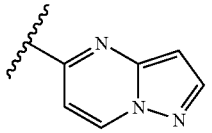 | 358.3 |
TABLE 1-continued
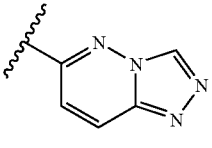
| Example | R¹ | MS (M + 1) |
|---|---|---|
| 27 | 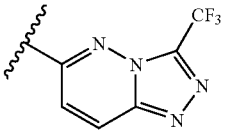 | 348.4 |
| 28 | 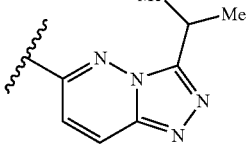 | 349.4 |
| 29 | 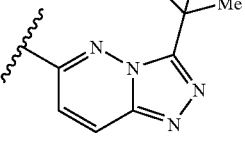 | 417.4 |
| 30 | 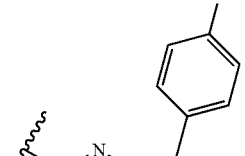 | 391.2 |
| 31 | 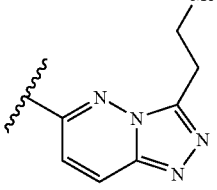 | 405.4 |
| 32 | | 443.2 |
| 33 | | 391.4 |

TABLE 1-continued
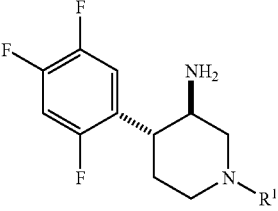
| Example | R[1] | MS (M + 1) |
|---|---|---|
| 34 | 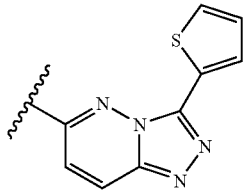 | 431.4 |
| 35 | 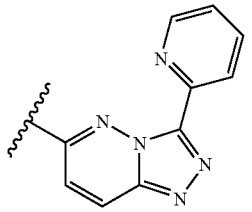 | 431.4 |
| 36 | 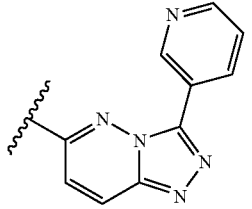 | 426.3 |
| 37 | 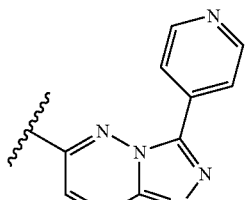 | 426.5 |
| 38 | 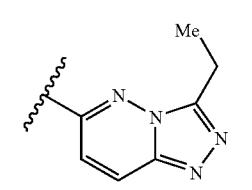 | 426.5 |
| 39 | 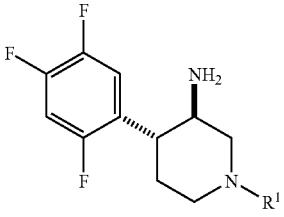 | 377.5 |
| 40 | 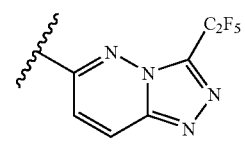 | 467.2 |
| 41 | 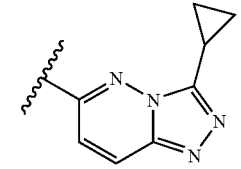 | 389.2 |
| 42 | 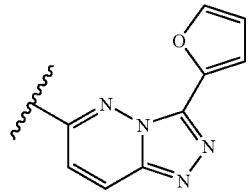 | 415.1 |
| 43 | 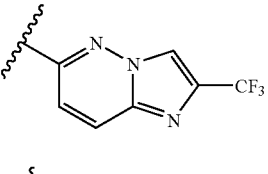 | 416.4 |
| 44 | 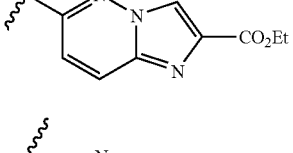 | 420.3 |
| 45 | 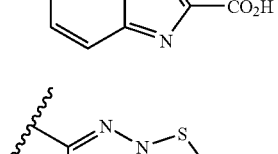 | 392.2 |
| 46 | 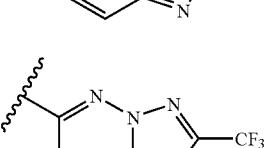 | 382.1 |
| 47 | | 417.2 |

TABLE 1-continued

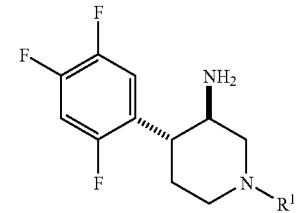

| Example | R¹ | MS (M + 1) |
|---|---|---|
| 48 | 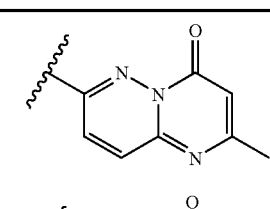 | 390.2 |
| 49 | 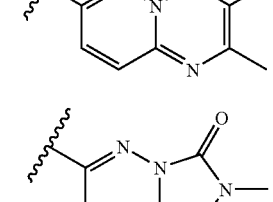 | 408.0 |
| 50 | 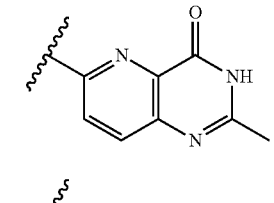 | 379.2 |
| 51 | 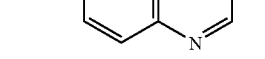 | 390.2 |
| 52 | 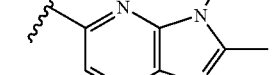 | 374.1 |
| 53 | 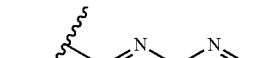 | 376.2 |
| 54 | 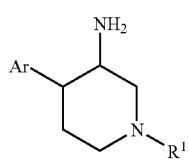 | 361.1 |

Example of a Pharmaceutical Formulation

As a specific embodiment of an oral pharmaceutical composition, a 100 mg potency tablet is composed of 100 mg of any of Example 1, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

(I)

$$\text{Ar} \underset{\underset{R^1}{N}}{\overset{NH_2}{\bigvee}}$$

or a pharmaceutically acceptable salt thereof; wherein
each n is independently 0, 1, 2 or 3;
Ar is phenyl unsubstituted or substituted with one to five $R^3$ substituents;
each $R^3$ is independently selected from the group consisting of
halogen,
cyano,
hydroxy,
$C_{1-6}$ alkyl, unsubstituted or substituted with one to five halogens, and
$C_{1-6}$ alkoxy, unsubstituted or substituted with one to five halogens;
$R^1$ is heteroaryl unsubstituted or substituted with one to four $R^2$ substituents, wherein the heteroaryl is selected from the group consisting of

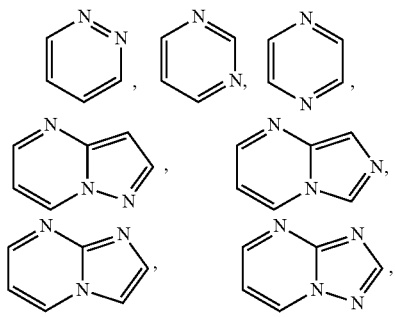

-continued

[chemical structures]

and each R² is independently selected from the group consisting of hydroxy, halogen, cyano, nitro, $C_{1-10}$ alkoxy, wherein alkoxy is unsubstituted or substituted with one to five substituents independently selected from halogen or hydroxy, $C_{1-10}$ alkyl, wherein alkyl is unsubstituted or substituted with one to five substituents independently selected from halogen or hydroxy, $C_{2-10}$ alkenyl, wherein alkenyl is unsubstituted or substituted with one to five substituents independently selected from halogen or hydroxy, $(CH_2)_n$-aryl, wherein aryl is unsubstituted or substituted with one to five substituents independently selected hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$—COOH, $(CH_2)_n$—COOC$_{1-6}$ alkyl, $(CH_2)_n$—NR$^4$R$^5$, $(CH_2)_n$—CONR$^4$R$^5$, $(CH_2)_n$—OCONR$^4$R$^5$, $(CH_2)_n$—SO$_2$NR$^4$R$^5$, $(CH_2)_n$—SO$_2$R$^6$, $(CH_2)_n$—NR$^7$SO$_2$R$^6$, $(CH_2)_n$—NR$^7$CONR$^4$R$^5$, $(CH_2)_n$—NR$^7$COR$^7$, and $(CH_2)_n$—NR$^7$CO$_2$R$^6$;

wherein any individual methylene (CH$_2$) carbon atom in $(CH_2)_n$ is unsubstituted or substituted with one to two groups independently selected from halogen, hydroxy, $C_{1-4}$ and $C_{1-4}$ alkoxy, wherein alkyl and alkoxy are unsubstituted or substituted with one to five halogens;

R$^4$ and R$^5$ are each independently selected from the group consisting of hydrogen, $(CH_2)_n$-phenyl, $(CH_2)_n$—$C_{3-6}$ cycloalkyl, and $C_{1-6}$ alkyl;

wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or R$^4$ and R$^5$ substituents together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;

each R$^6$ is independently $C_{1-6}$ alkyl, wherein alkyl is unsubstituted or substituted with one to five substituents independently selected from halogen and hydroxyl; and R$^7$ is hydrogen or R$^6$.

2. The compound of claim 1 wherein R$^3$ is selected from the group consisting of fluorine, chlorine, bromine, methyl, trifluoromethyl, and trifluoromethoxy.

3. The compound of claim 1 wherein said heteroaryl group $R^1$ is selected from the group consisting of:

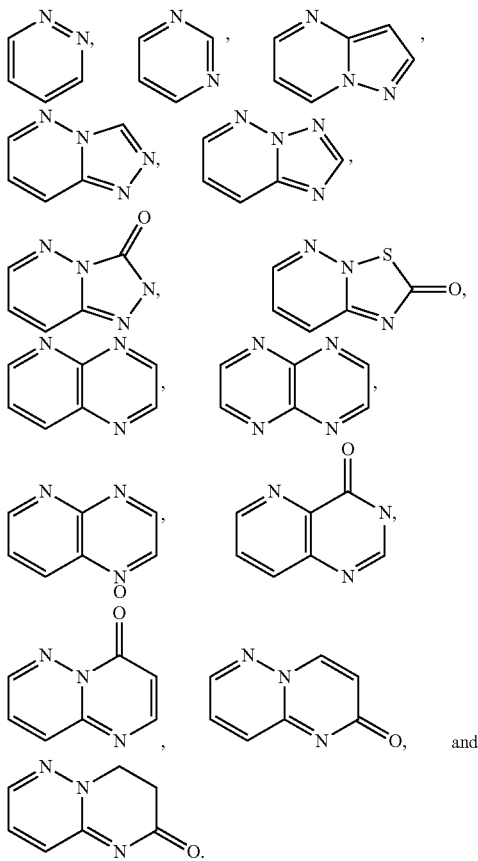

4. The compound of claim 3 wherein said heteroaryl group $R^1$ is selected from the group consisting of:

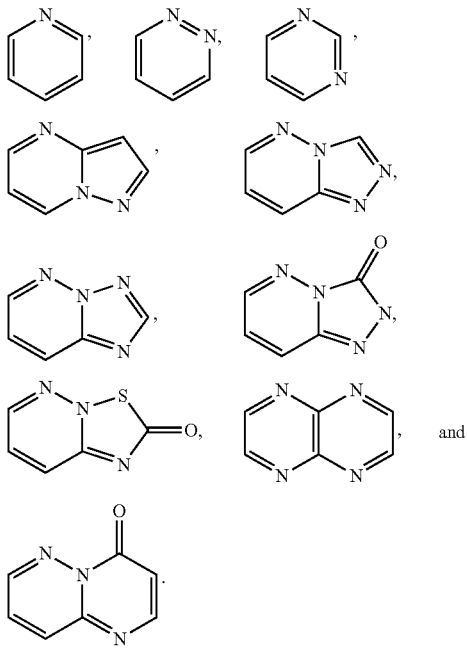

5. The compound of claim 4 wherein said heteroaryl group $R^1$ is selected from the group consisting of:

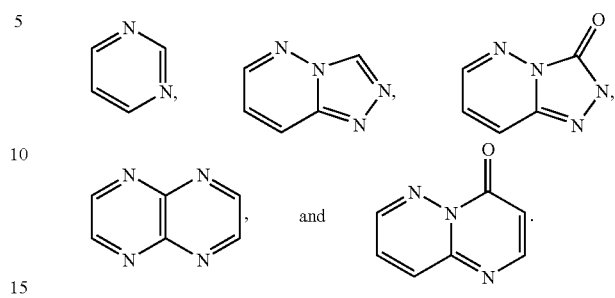

6. The compound of claim 1 wherein $R^2$ is selected from the group consisting of halogen, cyano, nitro, $C_{1-10}$ alkoxy, wherein alkoxy is unsubstituted or substituted with one to five substituents independently selected from halogen or hydroxy, $C_{1-10}$ alkyl, wherein alkyl is unsubstituted or substituted with one to five substituents independently selected from halogen or hydroxy, aryl, wherein aryl is unsubstituted or substituted with one to five substituents independently selected hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, heteroaryl, wherein heteroaryl is unsubstituted or substituted with one to three substituents independently selected from hydroxy, halogen, cyano, nitro, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, and $C_{3-6}$ cycloalkyl, wherein cycloalkyl is unsubstituted or substituted with one to three substituents independently selected from halogen, hydroxy, cyano, nitro, COOH, $C_{1-6}$ alkoxycarbonyl, $C_{1-6}$ alkyl, and $C_{1-6}$ alkoxy, wherein said alkyl and alkoxy are unsubstituted or substituted with one to five halogens.

7. The compound of claim 6 wherein $R^2$ is selected from the group consisting of:

fluoro, chloro, cyano, nitro, $C_{1-4}$ alkyl, trifluoromethyl, methoxy, 4-fluorophenyl, cyclohexyl, and thienyl.

8. The compound of claim 1 of structural formulae Ia and Ib having the indicated stereochemical configuration at the two stereogenic piperidine carbon atoms marked with an *:

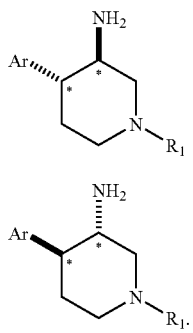

(Ia)

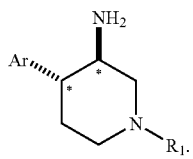

(Ib)

9. The compound of claim 8 of structural formula Ia having the indicated absolute stereochemical configuration at the two stereogenic piperidine carbon atoms marked with an *:

(Ia)

10. The compound of claim 9 wherein Ar is phenyl unsubstituted or substituted with one to three R³ substituents independently selected from fluorine and trifluoromethyl; and R¹ is a heteroaryl group selected from the group consisting of:

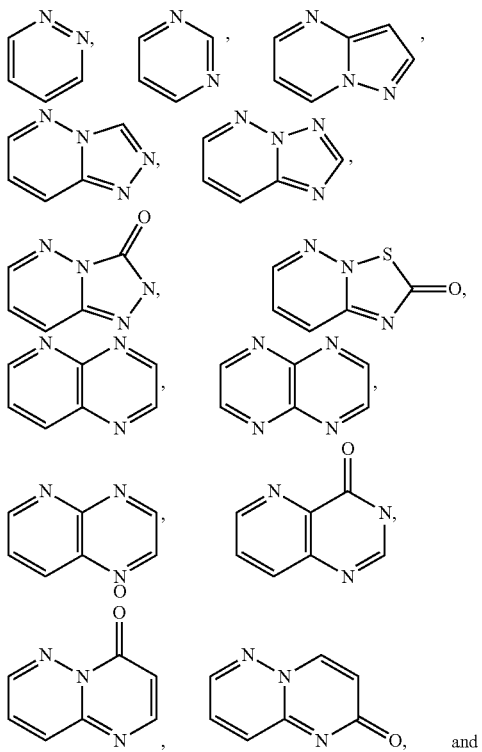

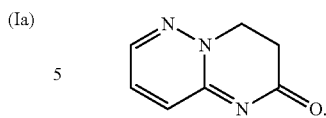

-continued wherein said heteroaryl group is unsubstituted or substituted with one to two R² substituents independently selected from the group consisting of:

fluoro,
chloro,
cyano,
nitro,
$C_{1-4}$ alkyl,
trifluoromethyl,
methoxy,
4-fluorophenyl,
cyclohexyl, and
thienyl.

11. The compound of claim 10 wherein said heteroaryl group R¹ is selected from the group consisting of:

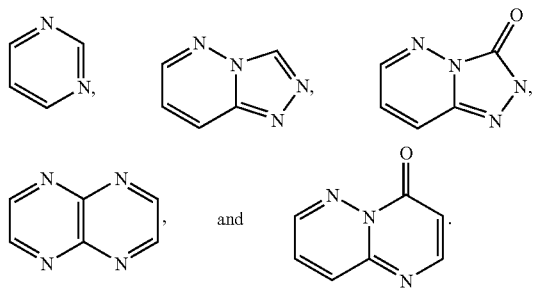

12. The compound of claim 10 which is selected from the group consisting of:

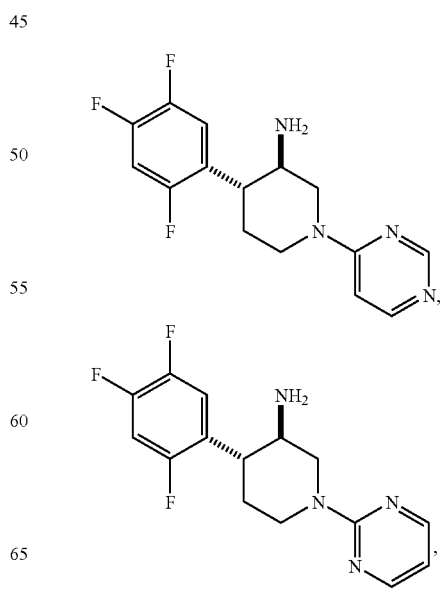

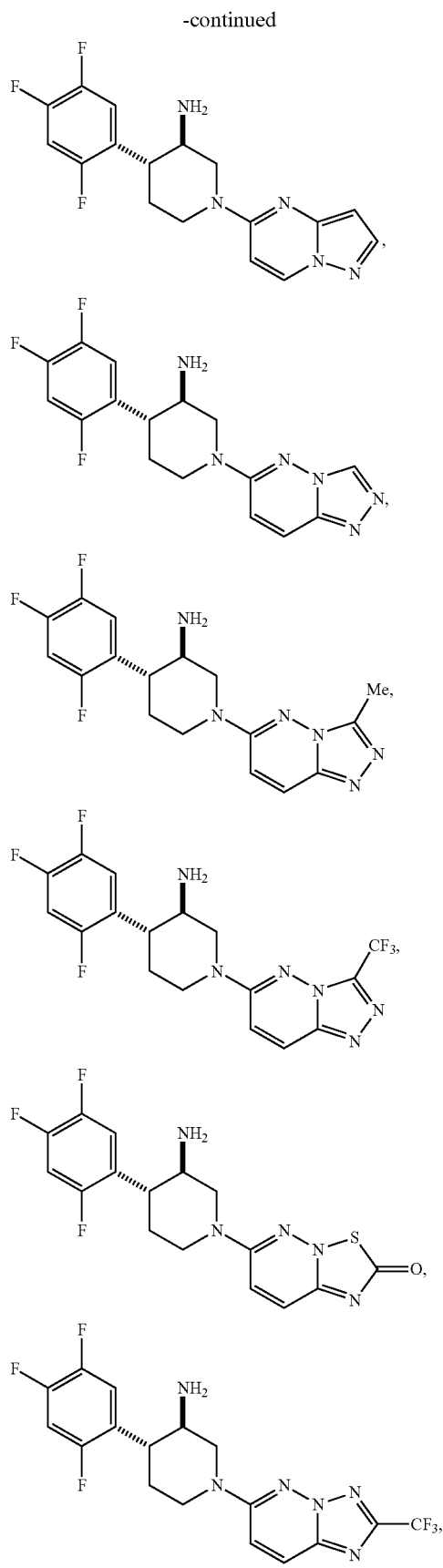
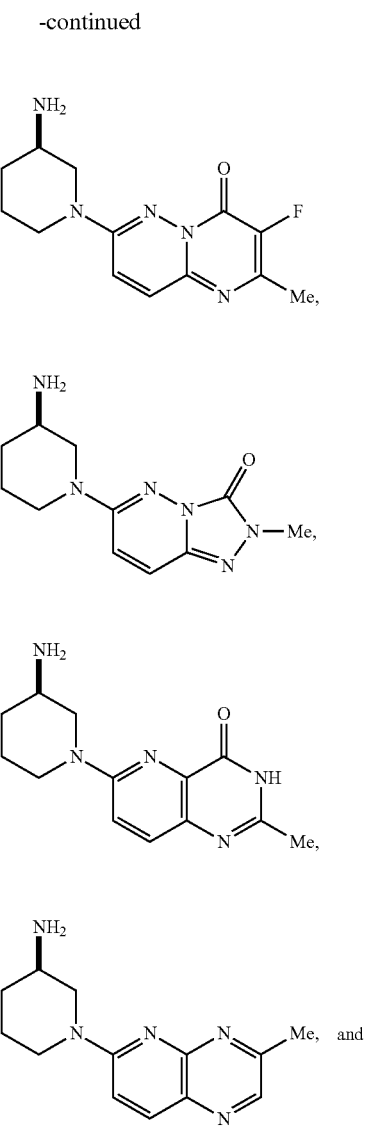

or a pharmaceutically acceptable salt thereof.

13. A pharmaceutical composition which comprises a compound of claim 1 and a pharmaceutically acceptable carrier.

14. The pharmaceutical composition of claim 13 additionally comprising metformin.

15. A method for treating non-insulin dependent (Type 2) diabetes in a mammal in need thereof which comprises the administration to the mammal of a therapeutically effective amount of a compounds of claim 1.

* * * * *

UNITED STATES PATENT AND TRADEMARK OFFICE
CERTIFICATE OF CORRECTION

| | | |
|---|---|---|
| PATENT NO. | : 7,884,104 B2 | Page 1 of 1 |
| APPLICATION NO. | : 11/662064 | |
| DATED | : February 8, 2011 | |
| INVENTOR(S) | : Jason M. Cox et al. | |

It is certified that error appears in the above-identified patent and that said Letters Patent is hereby corrected as shown below:

On the first page, at Paragraph (75), delete "Bart Harper, New York, NJ (US)"

On the first page, at Paragraph (75), add -- Bart Harper, New York, NY (US) --

Signed and Sealed this

Nineteenth Day of April, 2011

David J. Kappos
*Director of the United States Patent and Trademark Office*